(12) United States Patent
O'Connor et al.

(10) Patent No.: US 7,285,391 B2
(45) Date of Patent: Oct. 23, 2007

(54) METHODS FOR PREDICTING PREGNANCY OUTCOME IN A SUBJECT BY HCG ASSAY

(75) Inventors: John O'Connor, New Rochelle, NY (US); Steven Birken, Dumont, NJ (US); Galina Kovalevskaya, Bronx, NY (US)

(73) Assignee: The Trustees of Columbia Univeristy in the City of New York, New York, NY (US)

( * ) Notice: Subject to any disclaimer, the term of this patent is extended or adjusted under 35 U.S.C. 154(b) by 0 days.

(21) Appl. No.: 10/931,956

(22) Filed: Sep. 1, 2004

(65) Prior Publication Data
US 2005/0042702 A1 Feb. 24, 2005

Related U.S. Application Data

(63) Continuation of application No. 09/311,428, filed on May 13, 1999, now Pat. No. 6,927,034, which is a continuation-in-part of application No. PCT/US99/02289, filed on Feb. 3, 1999, which is a continuation-in-part of application No. 09/017,976, filed on Feb. 3, 1998, now Pat. No. 6,500,627.

(51) Int. Cl.
*G01N 33/00* (2006.01)
*G01N 33/53* (2006.01)
*A61K 39/395* (2006.01)

(52) U.S. Cl. .......... 435/7.1; 435/7.5; 435/7.9; 435/7.92; 435/7.94; 436/501; 436/814; 436/818; 530/387.5; 530/388.24; 530/389.2; 424/130.1

(58) Field of Classification Search .............. 435/7.1, 435/7.5, 7.9, 7.92, 7.94; 436/501, 814, 818; 530/387.5, 388.24, 389.2; 424/130.1
See application file for complete search history.

(56) References Cited

U.S. PATENT DOCUMENTS

| | | | |
|---|---|---|---|
| 4,514,505 A | 4/1985 | Canfield et al. | |
| 5,260,421 A | 11/1993 | Chappel et al. | |
| 6,133,048 A | 10/2000 | Penfold et al. | |
| 6,339,143 B1 | 1/2002 | Krichevsky et al. | |
| 6,429,018 B1 * | 8/2002 | Cole et al. ............ | 436/87 |
| 6,500,627 B1 | 12/2002 | O'Connor et al. | |
| 6,927,034 B2 | 8/2005 | O'Connor et al. | |

FOREIGN PATENT DOCUMENTS

| | | |
|---|---|---|
| JP | 04300896 A | 10/1992 |
| WO | WO 88/04779 | 6/1988 |
| WO | WO 99/41584 | 8/1999 |
| WO | WO 00/70094 | 11/2000 |

OTHER PUBLICATIONS

Aoki et al. (Gan to Kagaku Ryoho, 2005, 32(3) 411-416) Abstract Only.*
Perkins et al. (American Family Physician, Sep. 15, 2003, 68(6), 1075-1082.*
Duffy (Critical Reviews in Clinical Laboratory Sciences, 2001, 38(3), 225-262).*
Zografos et al.(Int. J. Gynecol. Cancer, 2004, 14, 721-740).*
O'Connor et al. (Cancer Research, 48, 1361-1366, Mar. 1, 1988).*
Bogart et al., (1989) "Human Chorionic Gonadotropin Levels in Pregnanies with Aneuploid Fetuses", *Prenat.Diagn.* 9: 379-384.
Bogart et al., (1987) "Abnormal Maternal Serum Chorionic Gonadotropin Levels in Pregnancies with Fetal Chromosome Abnormalities", *Prenat.Diagn.* 7: 623-630.
Cole et al., (1997) "Oligosaccharide Variants of hCG-related Molecules: Potential Screening Markers for Down Syndrome", *Prenat. Diagn.* 17: 1188-1190.
Cole et al., (1998) "Hyperglycosylated hCG, A Potential Alternative To hCG in Down Syndrome Screening", *Prenat.Diagn.* 18: 926-933.
Cole et al., (1997) "Urine β-Core Fragment, a Potential Screening Test for Ectopic Pregnancy and Spontaneous Abortion", *Fetal. Diagn.Ther.* 12: 336-339.
Forest et al., (1995) "Screening for Down Syndrome During the First and Second Trimesters: Impact of Risk Estimation Parameters", *Clin.Biochem.* 28: 443-449.
Kovalevskaya et al., (1999) "Early Pregnancy Human Chorionic Gonadotropin (hCG) Isoforms Measured By An Immunometric Assay For Choriocarcinoma-like hCG", *J.Endocrinol.* 161: 99-106.
Spencer et al., (1996) "Urine Free beta-hCG and Beta Core in Pregnancies Affected by Down's Syndrome", *Prenat.Diagn.* 16: 605-613.
Spencer et al., (1993) "Stability of Intact Chorionic Gonadotropin (hCG) in Serum, Liquid Whole Blood, and Dried Whole-Blood Filter-Paper Spots: Impact on Screening for Down Syndrome by Measurement of Free β-hCG Subunit", *Clin.Chem.* 39: 1064-1068.
Spencer et al., (1997) "Biochemical Markers of Trisomy 21 in Amniotic Fluid", *Prenat.Diagn.* 17: 31-37.
Valerio et al., (1996) "Maternal Serum Screening of Fetal Chromosomal Abnormalities by AFP, UE3, hCG and free-βhCG", *Minerva. Ginecol.* 48: 169-173.
Wald et al., (1994) "Four-Marker Serum Screening For Down's Syndrome", *Prenat.Diagn.* 14: 707-716.
Wald et al., (1994) "First Trimester Biochemical Screening for Down's Syndrome", *Ann.Med.* 26: 23-29.

(Continued)

*Primary Examiner*—Long V. Le
*Assistant Examiner*—Lisa V. Cook
(74) *Attorney, Agent, or Firm*—John P. White; Cooper & Dunham LLP

(57) ABSTRACT

The present invention provides a method of predicting pregnancy outcome in a subject by determining the amount of an early pregnancy associated molecular isoform of hCG in a sample. The present invention further provides a method for determining the amount of early pregnancy associated molecular isoforms of human chorionic gonadotropin (hCG) in a sample. The present invention also provides a diagnostic kit for determining the amount of early pregnancy associated hCG in a sample. The present invention additionally provides an antibody which specifically binds to an early pregnancy associated molecular isoform of human chorionic gonadotropin. Finally, the present invention provides methods for detecting trophoblast or non-trophoblast malignancy in a sample.

6 Claims, 15 Drawing Sheets

OTHER PUBLICATIONS

Zimmermann et al., (1996) "Age-Independent Indices in Second-Trimester Serum Screening for Down's Syndrome Are Useless", *Prenat.Diagn.* 16: 79-82.

Birken et al., (1993) "Separation of Nicked Human Chorionic Gonadotropin (hCG), Intact hCG, and hCG Beta Fragment From Standard Reference Preparations and Raw Urine Samples", *Endocrinology* 133: 1390-1397.

Birken et al., (1996) "Metabolism of hCG and hLH to Multiple Urinary Forms", *Mol. Cell Endocrinol.* 125: 121-131.

Birken et al., (1996) "Isolation and Characterization of Human Pituitary Chorionic Gonadotropin", *Endocrinology* 137: 1402-1411.

Cole et al., (1993) "The Deactivation of hCG by Nicking and Dissociation", *J.Clin.Endocrinol.Metab.* 76: 704-710.

Cole et al., (1985) "The Structures of the Serine-linked Sugar Chains on Human Chorionic Gonadotropin", *Biochem.Biophys.Res. Commun.* 126: 333-339.

Ellish et al., (1996) "A Prospective Study of Early Pregnancy Loss", *Hum.Reprod.* 11: 406-412.

Hoermann et al., (1994) "Immunological Recognition and Clinical Significance of Nicked Human Chorionic Gonadotropin in Testicular Cancer", *Clin.Chem.* 40: 2306-2312.

Kovalevskaya et al., (1995) "HLH Beta Core Fragment Immunoreactivity in the Urine of Ovulating Women: A Sensitive and Specific Immunometric Assay for its Detection", *Endocrine* 3: 881-887.

O'Connor et al., (1994) "Recent Advances in the Chemistry and Immunochemistry of Human Chorionic Gonadotropin: Impact on Clinical Measurements", *Endocr.Rev.* 15: 650-683.

O'Connor et al., (1998) "Differential Urinary Gonadotropin Profiles in Early Pregnancy and Early Pregnancy Loss", *Prenat.Diagn.* 18: 1232-1240.

O'Connor et al., (1988) "Development of Highly Sensitive Immunoassays to Measure Human Chorionic Gonadotropin, its Beta-subunit, and Beta Core Fragment in the Urine: Application to Malignancies", *Cancer Res.* 48: 1361-1366.

Wilcox et al., (1988) "Incidence of Early Loss of Pregnancy", *N.Engl.J.Med.* 319: 189-194.

Zinaman et al., (1996) "Estimates of Human Fertility and Pregnancy Loss", *Fertil.Steril.* 65: 503-509.

Acevedo et al., (1992) "Expression of Membrane-associated Human Chorionic Gonadotropin, Its Subunits, and Fragments by Cultured Human Cancer Cells", *Cancer* 69(7): 1829-1842.

Berger et al., (1993) "Variants of Human Chorionic Gonadotropin from Pregnant Women and Tumor Patients Recognized by Monoclonal Antibodies", *J. Clin. Endocrinol. and Metabolism* 77(2): 347-351.

Birken et al., (1999) "Development and Characterization of Antibodies to a Nicked and Hyperglycosylated Form of hCG from a Choriocarcinoma Patient", *Endocrinology* 10(2): 137-144.

Cole et al., (1991) "The Heterogeneity of Human Chorionic Gonadotropin (hCG). III. The Occurrence and Biological and Immunological Activities of Nicked hCG", *Endocrinology* 129(3): 1559-1567.

Hoermann et al., (1993) "Molecular Heterogeneity of Human Chorionic Gonadotropin on Serum and Urine from Patients with Trophoblastic Tumors", *Clinical Investigation* 71:953-960.

Kovalevskaya et al., (1999) "Evaluation of Nicked Human Chorionic Gonadotropin Content in Clinical Specimens by a Specific Immunometric Assay", *Clinical Chemistry* 45(1):68-77.

Birken et al., (1993) "Separation of Nicked Human Chorionic Gonadotropin (hCG), Intact hCG, and hCGβ Fragment from Standard Reference Preparations and Raw Urine Samples", *Endocrinology* 133(3): 1390-1397.

Ellish et al., (1996) "A Prospective Study of Early Pregnancy Loss", *Human Reproduction* 11(2): 407-408.

Hoermann et al., (1994) "Immunological Recognition and Clinical Significance of Nicked Human Chorionic Gonadotropin in Testicular Cancer" *Clinical Chemistry* 40(12): 2306-2312.

Knight, (1989) "The Carbohydrate Frontier", *Biotechnology* 7(1): 35 and 39-40.

Cole, L.A. (1998) "hCG, its free subunits and its metabolites. Roles in pregnancy and trophoblastic disease," *J. Reproduction Med.* 43(1):3-10.

Huang, S., et al. (1998) "A chromatofocusing study of human chorionic gonadotropin in biological fluids in normal pregnancy, pre-eclampsia and choriocarcinoma," *J. Formos Med. Assoc.* 87:1036-44.

Kovalevskaya, G., et al. (2002) "Differential expression of human chorionic gonadotropin (hCG) glycosylation isoforms in failing and continuing pregnancies: preliminary characterization of the hyperglycosylated hCG epitope," *J. Endocrinology* 172:497-506.

Rau, B., et al. (1995) "Significance of beta-hCG in the serum as a tumor marker for gastric cancer," *Langenbecks Arch. Cher.* 380:359-64.

* cited by examiner

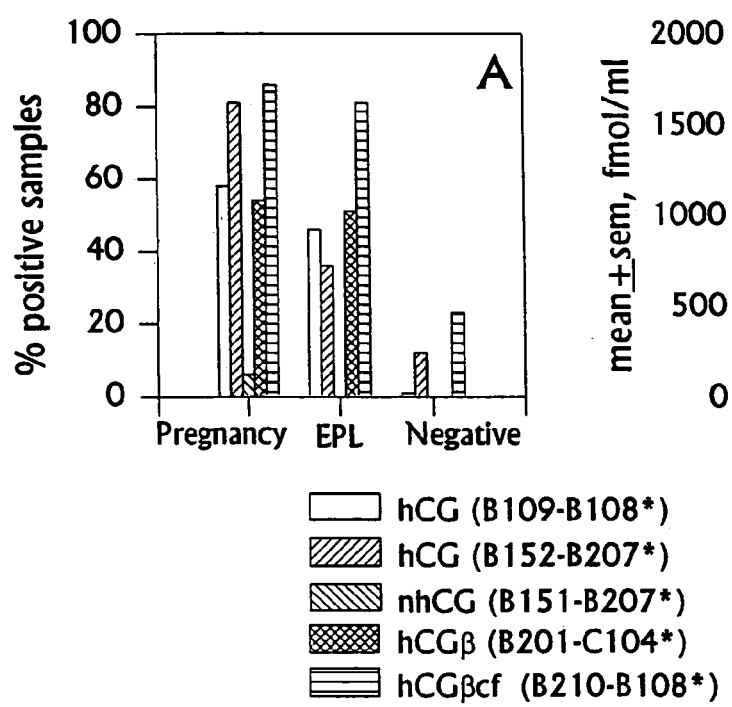
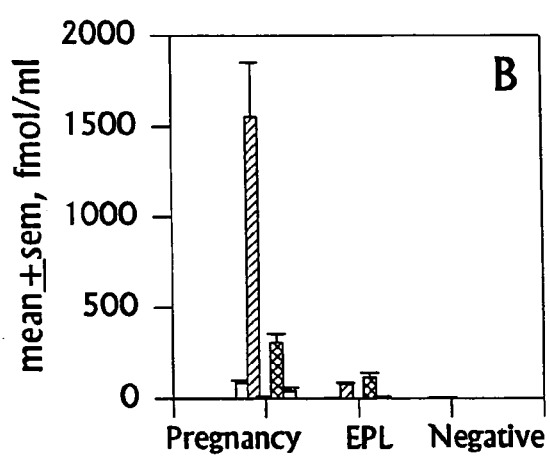
FIG. 2A
FIG. 2B

—●— choriocarcinoma hCG (C5)
—■— pregnancy hCG
—▲— pituitary hCG

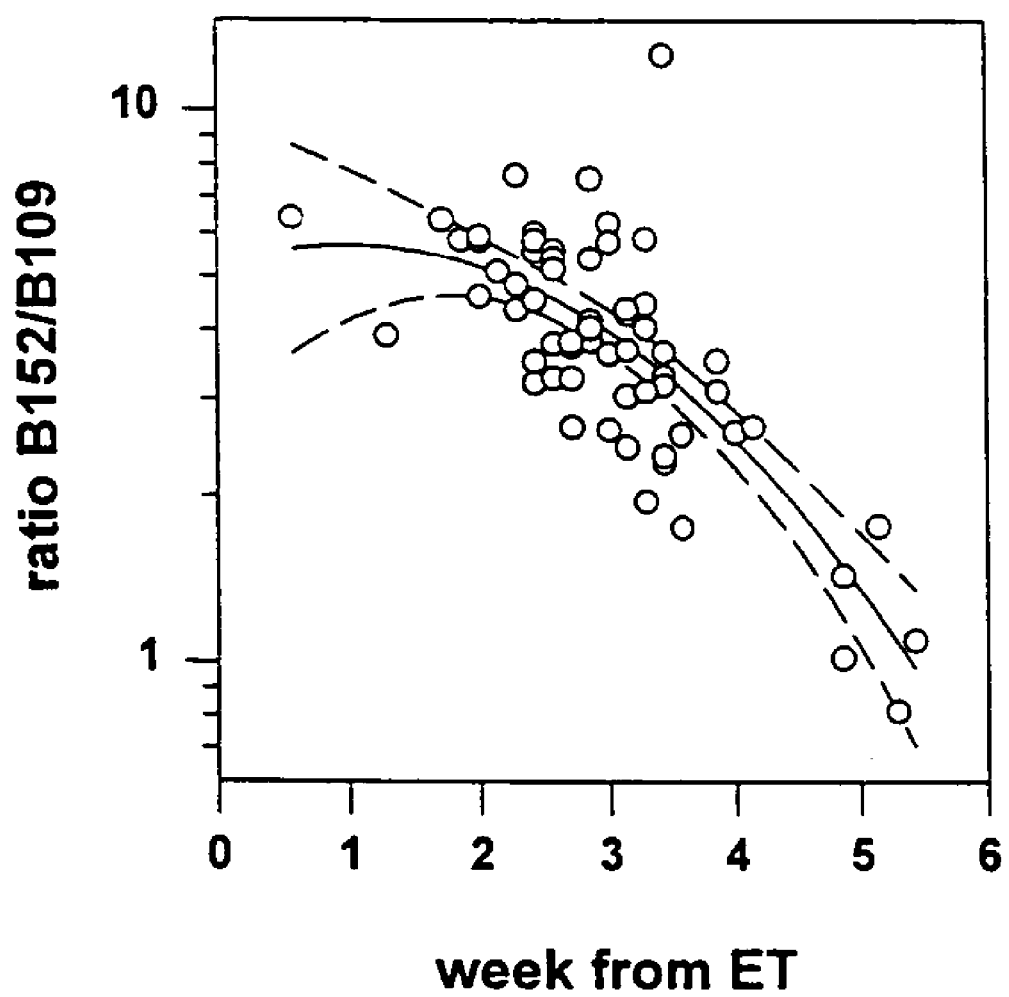

• B109-B108*   ▲ B152-B207*   ◆ B210-B108*
■ B151-B207*   ▼ B201-C104*

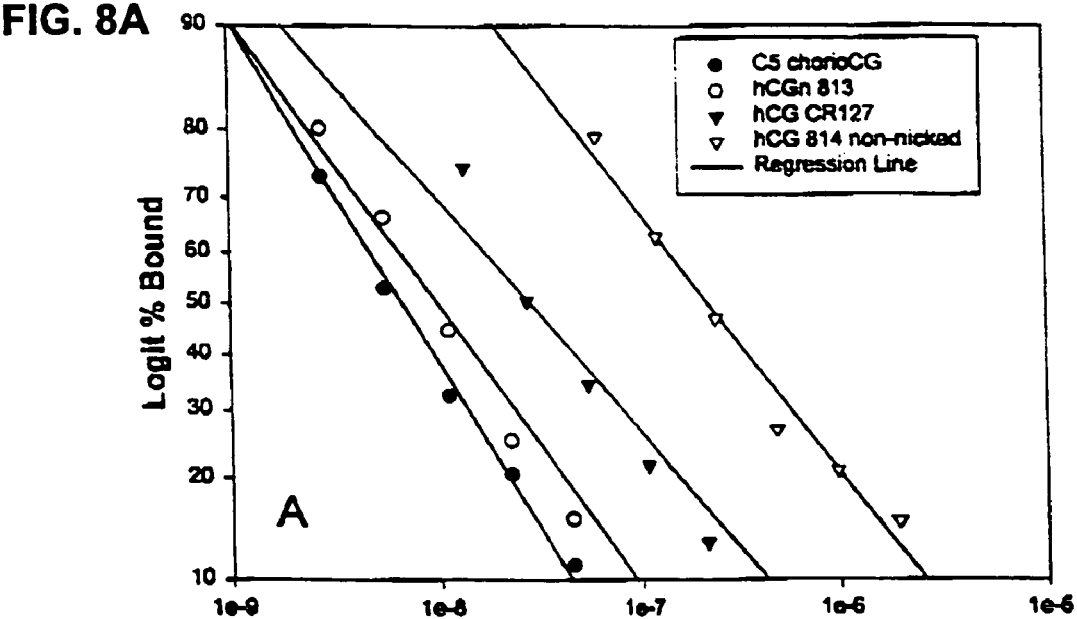
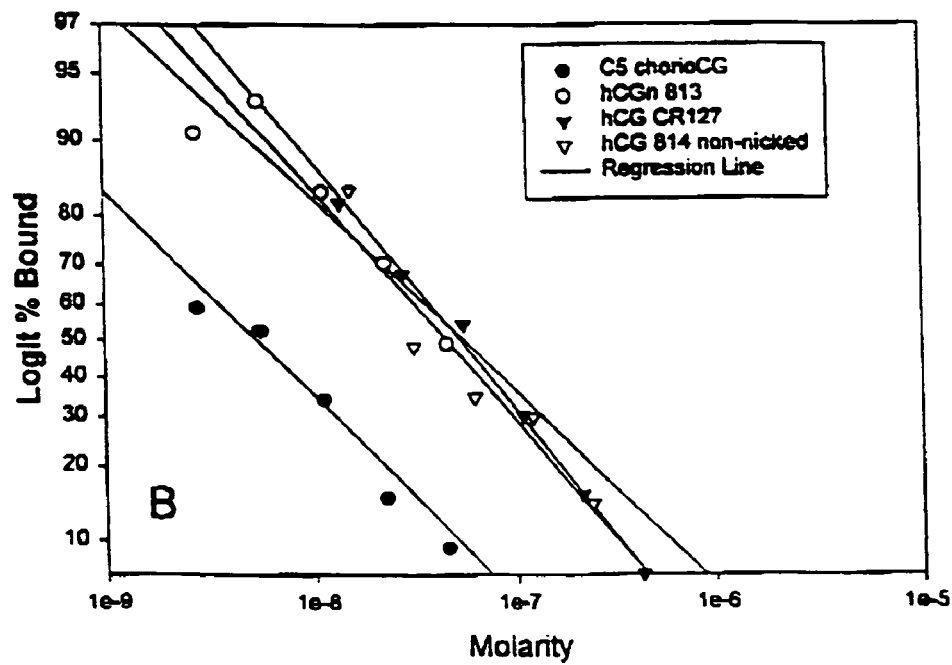

Dose (pmole/ml)

FIG. 11

Table 1. Characteristics of the Reagents Used to Define Antibody Specificity. The peptide and carbohydrate structures of the reagents used were determined earlier (26). The % nicked β-subunit refers to the proportion of molecules with cleavages (missing peptide bonds) in the region β43 to β48. The % tetrasaccharide core is the proportion of O-linked oligosaccharides with tetrasaccharide (vs. disaccharide) core structure, and the % sialic acid, is the proportion of O-linked structures with antennae terminated by sialic acid residues. The proportion of triantennary N-linked oligosaccharides on β-subunit is given, as is the corresponding % sialic acid

| Name | Source | N-Sialic acid [a] | O-Sialic acid [b] | % triantennary N-linked on β | % tetrasaccharide O-linked core | % β nicking |
|---|---|---|---|---|---|---|
| 814 hCG | CR 127 hCG [c] | 95 | 66 | 5 | 19 | 19 |
| C5 chorioCG | Choriocarcinoma | 95 | 58 | 48 | 100 | 100 |
| M4 mole CG | Mole pregnancy | 120 | 49 | 30 | 20 | 98 |
| 813 hCGn | CR 127 hCG | ND | ND | ND | ND [d] | 80 |
| C7 chorioCG | Choriocarcinoma | 68 | 53 | 48 | 69 | 3 |
| P8 hCG | Pregnancy | 94 | 73 | 21 | 13 | 0 |
| M4 mole β | Mole pregnancy | 120 | 49 | 30 | 20 | 98 |
| C5 chorio β | C5 chorioCG | 95 | 58 | 48 | 100 | 100 |
| CR 129 β | CR 129 hCG | 96 | 63 | 11 | 17 | 19 |
| HLH 1-1 | Pituitary hLH | ND | NA [d] | NA | NA | NA |
| M1A | Mole pregnancy | 98.5 | NA | 16.5 | <15% CTP [e] | 24 |

[a] % sialic acid residues per sugar chain, N-linked on β.
[b] % sialic acid residues per sugar chain, O-linked on β.
[c] The "CR" series of hCG reference preparations were made at Columbia University and were distributed internationally as reference materials for purified hCG. CR 119 is also known as the 3rd international immunoassay reference preparation for hCG.
[d] ND is not done; NA is not applicable to that reagent.
[e] Less than 15% of the beta COOH-terminal region is present on this preparation.

FIG. 12

Table II: Affinity Constants[a] Determined by Liquid Phase Competition Assays Using C5 as Tracer Ligand

| Antibody | C5 chorioCG | Nicked hCG CR 127 (813) | Parent CR 127 hCG[b] | Nick-free hCG CR127 (814) |
|---|---|---|---|---|
| B151 | $4.4 \times 10^8$ | $3.8 \times 10^8$ | $4.2 \times 10^7$ | $1.3 \times 10^7$ |
| B152 | $3.5 \times 10^9$ | $5.4 \times 10^7$ | $4.7 \times 10^7$ | $5 \times 10^7$ |

[a] Ka as L/M

[b] hCG CR 127 is an NIH-distributed hCG reference preparation produced at Columbia University.

FIG. 13A

Table III: Matrices of data for binding characteristics of different pairs of detection antibodies using B151 or B152 as capture antibody.

A. Relative Cross-Reactivities of Two Site Assay Using B151 as Capture Antibody

| Ligand | B207[a,c] | B204[a] | B201[a] | B108[a] | B109[a] | A109[a] | CTP104 |
|---|---|---|---|---|---|---|---|
| C5 | 100% | <[b] | ∨ | 100% | ∨ | ∨ | 100 |
| 813 CR 127 hCGn | 100% | ∨ | ∨ | 100% | ∨ | ∨ | 47% |
| 814 CR127 hCG | 12% | ∨ | ∨ | 37% | ∨ | ∨ | 14% |
| HCGβ | 2% | ∨ | ∨ | 2% | ∨ | ∨ | ∨ |
| C5 β | 5% | ∨ | ∨ | | ∨ | ∨ | ∨ |
| HCGβ core | ∨ | ∨ | ∨ | | ∨ | ∨ | ∨ |
| HLH | 2% | ∨ | ∨ | 3% | ∨ | ∨ | ∨ |
| HLHβ | 5% | ∨ | ∨ | 3% | ∨ | ∨ | ∨ |
| HCG α | ∨ | ∨ | ∨ | 13% | ∨ | ∨ | 83% |
| Maximum binding[b] | 50% | 0% | 0% | | 0% | 0% | |

[a] labeled detection antibodies
[b] out of low range detection
[c] this particular assay format was applied in O'Connor et al (25).

FIG. 13B

B. Relative Cross-Reactivities of Two Site Assay Using B152 as Capture Antibody

| Ligand | B207[d] | B204[a] | B201[a] | B108[a] | B109[a] | A109[a] | CTP104[a] |
|---|---|---|---|---|---|---|---|
| C5 | 100% | 100% | 94% | 42% | 53% | 100% | <[c] |
| 813 CR 127 hCGn | 10% | <[b] | < | 15% | 32% | 64% | < |
| 814 CR127 hCG | 7% | < | < | 30% | 100% | 26% | < |
| HCG β | 6% | 20% | 19% | 11% | < | < | < |
| C5 β | 190% | 100% | 100% | 100% | < | < | < |
| HCGβ core | <1% | < | < | < | < | < | < |
| HLH | <1% | < | < | < | < | < | < |
| hLHβ | <1% | < | < | < | < | < | < |
| HCG α | 64% | 2% | 44% | 80% | 2% | 14% | < |
| Maximum binding[b] | | | | | | | 25% |

The molar quantity of ligand required to produce binding equal to 50% of the maximum binding achieved by C5 was determined. Cross-reactivity shown in this table as a percentage is calculated by dividing the molar quantity of the standard by the molar quantity of the other ligand at 50% maximum binding dose.

[a] labeled detection antibodies

[b] maximum binding represents the total quantity of radiolabeled detection antibody which can bind to the plate in the system described.

[c] < out of low range detection

[d] this particular assay format was applied in O'Connor et al (25)

FIG. 14

Table IV. Immunoreactivity of antigens in the B152 immunoradiometric assay. The dose-response curves used to provide data for this table are shown in Figure 3. Each curve was fitted with 4-5 points. Slope and coefficient of determination ($R^2$) were determined using a non-linear regression algorithm. Slopes were used as an indicator of antigen potency. Relative potency was estimated as the slope of antigens relative to the slope of C5 Choriocarcinoma hCG (the immunogen)

| Reagent | Slope[a] | S.E. | $R^2$ | Relative Potency |
|---|---|---|---|---|
| 814 hCG | 0.1588 | 0.0098 | 0.992 | 10.2% |
| C5 chorioCG | 1.5603 | 0.1015 | 0.983 | 100% |
| M4 mole hCGn | 0.5317 | 0.0240 | 0.992 | 34% |
| 813 hCGn | 0.0986 | 0.0021 | 0.999 | 6.3% |
| C7 chorioCG | 1.4515 | 0.1246 | 0.985 | 93.0% |
| P8 hCG | 0.2192 | 0.0031 | 0.999 | 14.0% |
| M4 mole hCGβ | 0.1038 | 0.0069 | 0.991 | 6.67% |
| C5 chorioCGβ | 0.1286 | 0.0042 | 0.998 | 8.24% |
| CR 129 hCGβ | Only 2 points | | | |
| HLH batch I-1 | No response | | | |

[a] Slope are from figure 3 as calculated in Sigmaplot 4.01 by linear regression analysis. Units of slope are pmole/ml absorbance at 492nm.

METHODS FOR PREDICTING PREGNANCY OUTCOME IN A SUBJECT BY HCG ASSAY

This application is a continuation of U.S. Ser. 09/311,428, filed May 13, 1999, now U.S. Pat. No. 6,927,034, which is a continuation-in-part application of International Application No. PCT/US99/02289, filed Feb. 3, 1999, which is a continuation-in-part of U.S. Ser. No. 09/017,976, filed Feb. 3, 1998, now U.S. Pat. No. 6,500,627, the contents of which are hereby incorporated by reference into this application.

The invention disclosed herein was made with United States Government support under National Institutes of Health Grant Nos. NIEHS ES-07589 and HD 15454. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art.

Early pregnancy loss (EPL) is a widespread, but largely undiagnosed problem. In order to adequately diagnose and develop treatments for EPL it is essential to be able to detect and measure the rate of occurance of EPL. This is critically important in epidemiological studies, some of which are related to exposures to known or suspected reproductive toxins in the workplace, in the environment or by personal use. These early pregnancy losses are often not recognized by women or physicians and are detected solely by the measurement of hCG in the urine at the time between implantation and expected menses. They are sometimes termed "chemical pregnancies" or "occult pregnancies." A landmark epidemiological study established that the incidence of EPL was 22% in a population of healthy women attempting to conceive (Wilcox, A. J., et al., 1988). This investigation employed a very sensitive (0.01 ng/ml hCG) assay which detected only the intact hCG molecule with the unique beta subunit carboxyterminal peptide present.

There are multiple likely causes for EPL and clinical spontaneous abortion including genetic abnormality, immunological dysfunction, untreated infection or other unknown physiological problems. In addition, losses may be caused by failure of human chorionic gonadotropin (hCG) to induce adequate response at its target, the corpus luteum. This could result from inadequate hormonal potency. "Nicking" of the beta subunit in the loop 2 region of the molecule, specifically between residues 44-49, can reduce biopotency of hCG. Cleaved peptide bonds in this area of the molecule also exhibit reduced biopotency and reduced immunochemical recognition by monoclonal antibodies directed to the heterodimeric hormone (Cole, L. A., et al., 1991a; Cole , L. A., et al., 1991b; Puisieux, A., et al., 1990; Nishimura, R., et al., 1988; Nishimura, R. T., et al., 1989). Nicked forms of hCG were examined as possibly more prevalent in EPL situations and, at least in part responsible, for early pregnancy loss. Unfortunately many of the reports claiming that substantial ccncentrations of nicked hCG are produced during pregnancy, losses or successful pregnancies, are not accurate due to faulty assumptions regarding assay specificity (Wilcox, A. J., et al., 1988). Carbohydrate-modified hCG can also exhibit reduced biopotency. It is known that if the hCG has much reduced sialic acid content and its carbohydrate chains terminate in galactose, much hCG would be removed by the liver receptor for such altered glycoproteins (Braun, J. R., et al., 1996; Kawasaki, T. and G. Ashwell, 1996). The circulating life-time of asialo hCG is reduced and its in vivo potency is thereby low. Other carbohydrate changes also alter circulating half life; glycoproteins terminating in sulfate-N-acetyl galactosamine are also extracted by a specific liver receptor and have reduced circulating lifetime (Baenziger, J. U., 1994; Fiete, D., et al., 1991).

At least two factors affect increased potency of hCG. First, it is known that a larger Stoke's radius will decrease clearance through the kidney glomerulus which generally. clears proteins above an effective size of 70,000 very slowly. The effective size of urinary-isolated hCG is just at this borderline reduced clearance size. Generally, extra sugar content makes the hydrated radius of glycoproteins larger. It has been shown that by adding the hCG beta COOH-terminal peptide to hFSH or hLH, their circulating life-times greatly increased (Fares, F. A. et al., 1992; Matzuk, M. M., 1990). This addition was thought mostly due to the carbohydrate content of that peptide rather than simply the extra polypeptide size (Wilcox, A. J., et al., 1988). Second, increased negative charge of a protein will prolong its circulating time because of decreased renal clearance (Chmielewski, C. 1992, Quadri, K. H., et al., 1994; Maack, T., et al., 1985). This increased negative charge can be due to extra sialic acid or other negative groups, including sulfate such as is present on hLH and on the pituitary form of hCG (Birken, S., et al., 1996b). Changes which affect signal transduction at the receptor may also affect biopotency of hCG. It is known that deglycosylated hCG has much reduced receptor potency (Ravindranath, N., et al., 1992; Sairam, M. R., and L. G., Jiang, 1992; Browne, E. S., et al., 1990; Sairam, M. R., 1989; Sairam, M. R., et al., 1988). Carbohydrate reduced forms of hCG also have reduced signal transduction (Amano, J., et al., 1990; Bahl, O. P., et al., 1995; Moyle, W. R., 1975).

According to the present invention EPL or recurrent spontaneous abortion is not due to an abnormal hCG form that has reduced potency, such as nicked hCG. Instead, the present invention provides evidence that in successful outcome pregnancies women usually produce forms of hCG which are very highly potent in very early pregnancy; the standard urinary reference preparations of hCG are less potent forms of the hormone produced later in pregnancy. The increased potency could be caused by a combination of factors from circulating half-life to increased receptor affinity or signal transduction or all of the preceding. Since hCG is low very early in pregnancy, it is logical to find a more potent form of hCG on a molar basis to carry out its function until production levels rise as the trophoblastic cellular mass increases. The present invention describes molecular and immunological tools and methods including an antibody, B152, described herein which recognizes the highly potent early pregnancy associated molecular isoforms of hCG. The determination of blood and urine profiles for the B152 hCG isoforms throughout healthy pregnancies can delineate the pattern of isoforms in successful pregnancies. These isoforms can be measured by immunoassay alone, obviating the need to perform complex isoelectric focusing studies or other separation techniques. Additionally, the methods described herein are applicable to large numbers of samples.

SUMMARY OF THE INVENTION

The present invention provides a method of predicting pregnancy outcome in a subject by determining the amount of an early pregnancy associated molecular isoform of hCG in a sample comprising: (a) contacting a sample with an antibody which specifically binds to the early pregnancy associated molecular isoform of hCG under conditions permitting formation of a complex between the antibody and the early pregnancy associated molecular isoform of hCG; (b) measuring the amount of complexes formed, thereby determining the amount of the early pregnancy associated molecular isoform of hCG in the sample; and (c) comparing the amount early pregnancy associated molecular isoform of hCG in the sample determined in step (b) with either (i) the amount determined for temporally matched, normal pregnant subject(s) or (ii) the amount determined for non-pregnant subject(s), wherein the relative absence of the early pregnancy associated molecular isoform of hCG in the sample indicates a negative outcome of pregnany for the subject.

The present invention further provides a method of predicting pregnancy outcome in a subject by determining the amount of an early pregnancy associated molecular isoform of hCG in a sample comprising: (a) contacting a capturing antibody which specifically binds to the early pregnancy associated molecular isoform of hCG with a solid matrix under conditions permitting binding of the antibody with the solid matrix; (b) contacting the bound matrix with the sample under conditions permitting binding of the antigen present in the sample with the capturing antibody; (c) separating the bound matrix and the sample; (d) contacting the separated bound matrix with a detecting antibody which specifically binds to hCG under conditions permitting binding of antibody and antigen in the sample; (e) measuring the amount of bound antibody on the bound matrix, thereby determining the amount of early pregnancy associated molecular isoform of hCG in the sample; and (f) comparing the amount early pregnancy associated molecular isoform of hCG in the sample determined in step (e) with either (i) the amount determined for temporally matched, normal pregnant subject(s) or (ii) the amount determined for non-pregnant subject(s), wherein amounts of the early pregnancy associated molecular isoform of hCG in the sample similar to amounts of early pregnancy associated molecular isoform of hCG in temporally matched pregnant samples indicates a positive outcome amounts of early pregnancy associated molecular isoform of hCG in the sample similar to amounts of early pregnancy associated molecular isoform of hCG in the non-pregnant samples indicates a negative outcome of pregnancy for the subject.

In addition, the present invention provides a method for determining the amount of early pregnancy associated molecular isoforms of in a sample comprising: (a) contacting the sample with an antibody which specifically binds to an early pregnancy associated molecular isoform of hCG under conditions permitting formation of a complex between the antibody and the early pregnancy associated molecular isoform of hCG; and (b) determining the amount of complexes formed thereby determining the amount of early pregnancy associated molecular isoform of hCG in the sample.

Further, the present invention provides a diagnostic kit for determining the amount of early pregnancy associated hCG is a sample comprising:. (a) an antibody which specifically binds to an early pregnancy associated molecular isoform; (b) a solid matrix to which the antibody is bound; and (c) reagents permitting the formation of a complex between the antibody and a sample.

The present invention additionally provides an antibody which specifically binds to an early pregnancy associated molecular isoform of human chorionic gonadotropin.

Further, the present invention provides a method for detecting non-trophoblast malignancy in a sample comprising: (a) contacting a sample with an antibody which specifically binds to the early pregnancy associated molecular isoform of hCG under conditions permitting formation of a complex between the antibody and the early pregnancy associated molecular isoform of hCG; (b) contacting the sample with a second antibody which specifically binds to intact non-nicked hCG without substantially cross-reacting with said antibody under conditions permitting formation of a complex between the antibody and the early pregnancy associated molecular isoform of hCG; (c) measuring the amount of complexes formed, thereby determining the amount of the early pregnancy associated molecular isoform of hCG in the sample; and (d) comparing the amount of early pregnancy associated molecular isoform of hCG in the sample determined in step (b) with the amount of early pregnancy associated molecular isoform of hCG in the sample determined in step (c) wherein a positive detection of early pregnancy associated molecular isoform detected in step (b) and a relative absence of the early pregnancy associated molecular isoform of hCG detected in step (c) indicates the presence of non-trophoblast malignancy in the sample.

Finally, the present invention provides a method for detecting gestational trophoblast disease in a sample from a subject comprising (a) (contacting a sample with an antibody which specifically binds to the early pregnancy associated molecular isoform of hCG under conditions permitting formation of a complex between the antibody and the early pregnancy associated molecular isoform of hCG; (b) contacting the sample with a second antibody which specifically binds to intact non-nicked hCG without substantially cross-reacting with said antibody under conditions permitting formatting of a complex between the antibody and the early pregnancy associated molecular isoform of hCG; (c) measuring the amount of complexes formed, thereby determining the amount of the early pregnancy associated molecular isoform of hCG in the sample due to binding with the first antibody, and late pregnancy associated molecular isoform of hCG in the sample due to binding with the second antibody; (d) determining the ratio of early pregnancy associated molecular isoform of hCG to late pregnancy associated molecular isoform of hCG in the subject; and (e) comparing the ratio of early pregnancy associated molecular isoform of hCG to late pregnancy associated molecular isoform of hCG in time sample determined in step (c) over time, wherein a continuing high ratio of early pregnancy associated molecular isoform of hCG to late pregnancy associated molecular isoform of hCG in the sample determined in step (c) indicates the presence of gestational trophoblast disease in the subject.

Bioassay for forms of hCG. This is data from recombinant CHO cells expressing the LH/CG receptor. The response factor is cAMP production. The x-axis is dose of one of four calibrated, pure hormones as described on graph legends. Expressed hCG has no nicks; choriocarcinoma hCG (C5) is 100% nicked; CR 127 was purified into a nick-free (non-nicked, intact) and nick-enriched fraction as shown.

FIG. 2

Incidence (Panel A) and expression level (Panel B) of hCG-related molecules in the positive samples for each of the analyses measured (In early normal pregnancy, n=214; EPL cycles, n=49; and negative cycles, n=297).

FIG. 3

Binding curves for three hCG types in the B152-B207* assay (upper panel) and the B109-B108* assay (lower panel).

FIG. 4

Ratio of hCG isoforms measured by the B152-B207* and B109-B108* assays in normal pregnancy urine (n=103) at different gestational ages. (Regression curve and 95% confidence intervals are shown, $r^2$=0.79). An inflection point in the curve occurs at approximately 29 weeks.

FIG. 5

Box plot of the B152/B109 ratio for pregnancy matched serum/urine at 5-6 weeks of gestational age (n=12); or at 36-39 weeks of gestational age (n=11) and in JAR cell supernatant. Box extends to the $25^{th}$ and $75^{th}$ percentile. The upper and lower symbols indicate the $90^{th}$ and $10^{th}$ percentile respectively. A solid line inside the box marks the value of the $50^{th}$ percentile.

FIG. 6

Ratio of hCG isoforms measured by the B152-B207* and B109-B108* in urine of IVF patients (n=65) (Regression curve and 95% confidence intervals are shown, $r^2$=0.59)

Figure 7A:
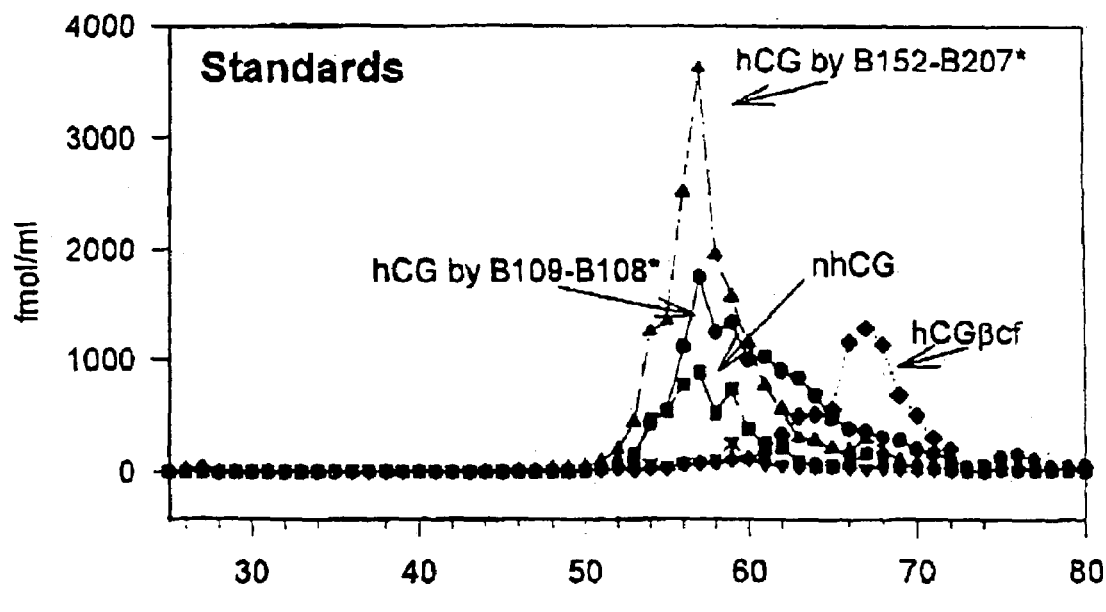
Figure 7B:
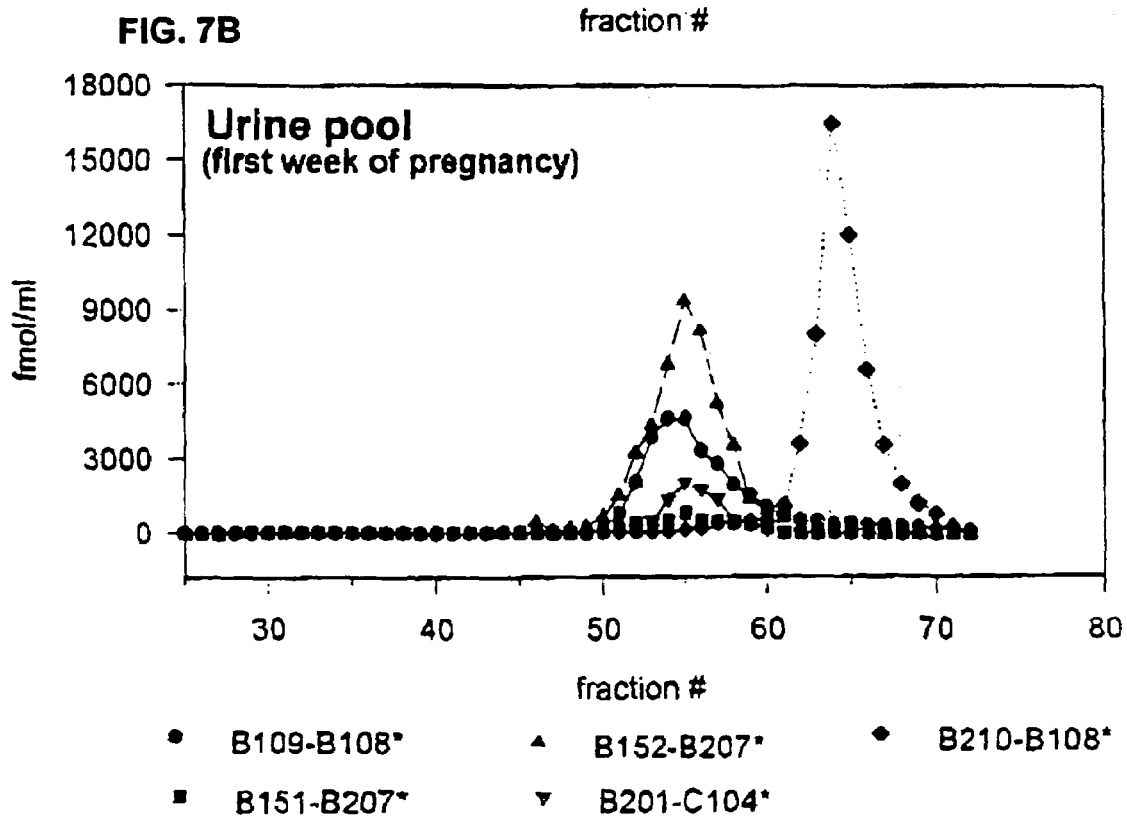

FIGS. 7A and 7B

Immunoassay profiles of fractions from SUPEROSE 12 column chromatography of a pooled urine concentrate from pregnant women.

FIG. 8

Liquid phase radioimmunoassays using antibody B151 (panel A) and antibody B152 (panel B). Radiolabeled choriocarciroma hCG was used as tracer and calibrated (by amino acid analysis) solutions of pregnancy C5 chorioCG, hCG CR 127, hCG CR 127 non-nicked, and hCGn CR 127 were employed as competitors. Non-linear regression lines were plotted in logit transformed format.

FIG. 9

Radio-Immunometric (two-site) assay using antibody B152 as capture and B207 as radiolabeled detection reagent. Binding curves are shown for competitors, various competitor as detailed in methods and results. Each panel represents a separate assay in which all ligands were introduced in the same assay. Points were connected by straight lines although regression analysis (4 parameter logistic) indicated excellent fit to logistic or sigmoidal curve shape: model. Panel A and B represent two distinct assays with similar results. It is clear that this assay has greatest recognition of the nicked, choriocarcinoma hCG immunogen which is hyperglycosylated and binds similarly to nicked and non-nicked forms of hCG which contain the usual quantities of sugars. Reagent M1A is missing most of its beta COOH-terminal region, supporting a role of this region in the binding site of B152 (see panel B and discussion in text).

FIG. 10

Enzymic-Immunometric (two-site) assay using antibody B152 as capture and peroxidase-labeled B4001 as detection antibody. A linear-linear plot of molar quantities of ligand added is plotted versus absorbance at 492 nm which is the response factor from the peroxidase detection system. Eight different hormone forms were measured as ligands and described in FIGS. 11 and 14. The two hyperglycosylated choriocarcinoma-derived hCG isoforms are both the most potent ligands (Table IV). Potency correlated well with hyperglycosylation of ligand (see FIGS. 11 and 14 and text)

FIG. 11

Characteristics of the Reagents Used to Define Antibody Specificity. The peptide and carbohydrate structures of the reagents used were determined earlier (26). The % nicked β-subunit refers to the proportion of molecules with cleavages (missing peptide bonds) in the region β43 to β48. The % tetrasaccharide core is the proportion of O-linked oligosaccharides with tetrasaccharide (vs. disaccharide) core structure, and the % sialic acid, is the proportion of O-linked structures with antennae terminated by sialic acid residues. The proportion of triantennary N-linked oligosaccharides on β-subunit is given, as is the corresponding % sialic acid.

.% sialic acid residue per sugar chain, N-linked on β.

.% sialic acid residues per sugar chain, O-linked on β.

[c] The "CR" series of hCG reference preparations were made at Columbia University and were distributed internationally as reference materials for purified hCG. CR 119 is also known as the $3^{rd}$ international immunoassay reference preparation for hCG.

[d] ND is not done; NA is not applicable to that reagent.

[e] Less than 15% of the beta COOH-terminal region is present on this preparation.

FIG. 12

Affinity Constants[a] Determined by Liquid Phase Competition Assays Using C5 as Tracer Ligand.

[a] Ka as L/M

[b] hCG CR 127 is an NIH-distributed hCG reference preparation produced at Columbia University.

FIG. 13

Matrices of data for binding characteristics of different pairs of detection antibodies using B151 or B152 as capture antibody.

A. Relative Cross-Reactivities of Two Site Assay Using B151 as Capture Antibody

[a] labeled detection antibodies

[b<] out of low range detection

[c] this particular assay format was applied in O'Connor et al (25).

B. Relative Cross-Reactivities of Two Site Assay Using B152 as Capture Antibody

The molar quantity of ligand required to produce binding equal to 50% of the maximum binding achieved by C5 was determined. Cross-reactivity shown in this figure as a percentage is calculated by dividing the molar quantity of the standard by the molar quantity of the other ligand at 50% maximum binding dose.

[a] labeled detection antibodies

[b] maximum binding represents the total quantity of radiolabeled detection antibody which can bind to the plate in the system described.

[c<] out of low range detection

[d] this particular assay format was applied in O'Connor et al (25).

FIG. 14

Immunoreactivity of antigens in the B152 immunoradiometric assay. The dose-response curves used to provide data for this figure are shown in FIG. 13. Each curve was fitted with 4-5 points. Slope and coefficient of determination (R2) were determined using a nonlinear regression algorithm. Slopes were used as an indicator of antigen potency. Relative potency was estimated as the slope of antigens relative to the slope of C5 Choriocarcinoma hGC (the immunogen)

[a] Slopes are from FIG. 13 as calculated in SIGMAPLOT 4.01 by linear regression analysis. Units of slope are pmole/ml absorbance at 492 nm.

DETAILED DESCRIPTION OF THE INVENTION

A method of predicting pregnancy outcome in a subject by determining the amount of an early pregnancy associated molecular isoform of hCG in a sample comprising: (a) contacting a sample with an antibody which specifically binds to the early pregnancy associated molecular isoform of hCG under conditions permitting formation of a complex between the antibody and the early pregnancy associated molecular isoform of hCG; (b) measuring the amount of complexes formed, thereby determining the amount of the early pregnancy associated molecular isoform of hCG in the sample; and (c) comparing the amount early pregnancy associated molecular isoform of hCG in the sample determined in step (b) with either (i) the amount determined for: temporally matched, normal pregnant subject (s) or (ii) the amount determined for non-pregnant subject(s), wherein the relative absence of the early pregnancy associated molecular isoform of hCG in the sample indicates a negative outcome of pregnancy for the subject. In an embodiment of the present invention, the antibody is B152. Another embodiment of this invention is the early pregnancy associated molecular isoform of Hcg.

The hybridoma producing the B152 monoclonal antibody was deposited on Feb. 3, 1998 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. The hybridoma, was accorded ATCC Accession Number HB-12467.

According to one embodiment of this invention, step (a) further comprises a second antibody which specifically binds to hCG without substantially cross-reacting with said antibody under conditions permitting formation of a complex between the antibody and the early pregnancy associated molecular isoform of hCG. In an embodiment of this invention, the second antibody is B207. According to another embodiment of this invention, step (a) further comprises a second antibody which specifically binds to intact non-nicked hCG without substantially cross-reacting with said antibody under conditions permitting formation of a complex between the antibody and the early pregnancy associated molecular isoform of hCG. In an embodiment of this invention, the second antibody is B108 or B109. In an embodiment of this invention, step (c) comprises comparing the amount of the early pregnancy associated molecular isoform of hCG determined in step (b) for said antibody with the amount determined in step (b) for the second antibody, wherein a high ratio of amounts determined for said antibody relative to the second antibody indicates a positive outcome of pregnancy for the subject, a low ratio indicates a negative outcome of pregnancy for the subject.

In yet another embodiment of this invention, step (c) comprises comparing the amount early pregnancy associated molecular isoform of hCG in the sample determined in step (b) with either (i) the amount determined for temporally matched, normal pregnant subject(s) or (ii) the amount determined for non-pregnant subject(s), wherein amounts of the early pregnancy associated molecular isoform of hCG in the sample similar to amounts of early pregnancy associated molecular isoform of hCG in temporally matched pregnant samples indicates a positive outcome, amounts of early pregnancy associated molecular isoform of hCG in the sample similar to amounts of early pregnancy associated molecular isoform of hCG in the non-pregnant samples indicates a negative outcome of pregnancy for the subject.

This invention also provides a method of predicting the likelihood of a negative pregnancy outcome in a female subject comprising: (a) contacting a sample from the subject with a capture antibody which specifically binds to an early pregnancy associated molecular isoform of hCG under conditions permitting formation of a complex between the antibody and the early pregnancy associated molecular isoform of hCG; (b) contacting any complex formed in step (a) with a labelled detection antibody under conditions permitting binding to the complex the capture antibody and the hCG isoform; (c) measuring the amount of labeled detection antibody bound to the complex so as to thereby determine the amount of the early pregnancy associated molecular isoform of hCG in the sample; and (d) comparing the amount early pregnancy associated molecular isoform of hCG in the sample determined in step (b) with the amount determined for a normal pregnant subject, wherein the relative absence of the early pregnancy associated molecular isoform of hCG in the sample indicates a negative outcome of pregnancy for the subject.

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

The present invention further provides a method of predicting pregnancy outcome in a subject by determining the amount of an early pregnancy associated molecular isoform of hCG in a sample comprising: (a) contacting a capturing antibody which specifically binds to the early pregnancy associated molecular isoform of hCG with a solid matrix under conditions permitting binding of the antibody with the solid matrix; (b) contacting the bound matrix with the sample under conditions permitting binding of the antigen present in the sample with the capturing antibody; (c) separating the bound matrix and the sample; (d) contacting the separated bound matrix with a detecting antibody which specifically binds to hCG under conditions permitting binding of antibody and antigen in the sample; (e) measuring the amount of bound antibody on the bound matrix, thereby determining the amount of early pregnancy associated molecular isoform of hCG in the sample; and (f) comparing the amount early pregnancy associated molecular isoform of hCG in the sample determined in step (e) with either (i) the amount determined for temporally matched, normal pregnant subject(s) or (ii) the amount determined for non-pregnant subject(s), wherein amounts of the early pregnancy associated molecular isoform of hCG in the sample similar to amounts of early pregnancy associated molecular isoform of hCG in temporally matched pregnant samples indicates a positive outcome, amounts of early pregnancy associated molecular isoform of hCG in the sample similar to amounts of early pregnancy associated molecular isoform of hCG in the non-pregnant samples indicates a negative outcome of pregnancy for the subject.

An embodiment of this invention further comprises (a) removing of the sample from the matrix; and (b) washing the bound matrix with an appropriate buffer. In one embodiment of this invention, the capturing antibody is B152. In one embodiment of this invention, the detecting antibody is B207. In an embodiment of this invention, step (a) further comprises a second capturing antibody which specifically binds to intact non-nicked hCG without substantially cross-reacting with said antibody under conditions permitting formation of a complex between the antibody and the early pregnancy associated molecular isoform of hCG. According to an embodiment of this invention, the second capturing antibody is B103 or B109. In an embodiment of this invention, step (d) further comprises a second detecting antibody which specifically binds to hCG without substantially cross-reacting with said antibody under conditions permitting formation of a complex between the antibody and the early pregnancy associated molecular isoform of hCG. In an embodiment of this invention, step (f) comprises comparing the amount of the early pregnancy associated molecular isoform of hCG determined in step (e) for said antibody with the amount determined in step (b) for the second antibody, wherein a high ratio of amounts determined for said antibody relative to the second antibody indicates a positive outcome of pregnancy for the subject, a low ratio indicates a negative outcome of pregnancy for the subject.

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

In addition, the present invention provides a method for determining the amount of early pregnancy associated molecular isoforms of in a sample comprising: (a) contacting the sample with an antibody which specifically bind to an early pregnancy associated molecular isoform of hCG under conditions permitting formation of a complex between the antibody and the early pregnancy associated molecular isoform of hCG; and (b) determining the amount of complexes formed thereby determining the amount of early pregnancy associated molecular isoform of hCG in the sample.

According to an embodiment of this invention, the antibody specifically binds a region of the early pregnancy associated molecular isoform of hCG comprising a carbohydrate moiety. In one embodiment of this invention the antibody is produced by a hybridoma cell line. In one embodiment of this invention the antibody is B152. In another embodiment the antibody specifically binds to the nicked form of human gonadotropin. The antibody is unlabeled or labeled with a detectable marker. In one embodiment of the invention the detectable marker is a detection antibody. In another embodiment the antibody specifically binds an epitope dependent upon peptide bond cleavage in beta loop 2. In still another embodiment the antibody binds the human gonadotropin at the beta COOH-terminal region.

Further, the present invention provides a diagnostic kit for determining the amount of early pregnancy associated hCG is a sample comprising: (a) an antibody which specifically binds to an early pregnancy associated molecular isoform; (b) a solid matrix to which the antibody is bound; and (c) reagents permitting the formation of a complex between the antibody and a sample. In an embodiment of this invention, the antibody is B108, B109 or B152. An embodiment of this invention further comprises control sample(s) normal pregnant sample(s), nonpregnant sample(s), or male sample(s).

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

The present invention additionally provides an antibody which specifically binds to an early pregnancy associated molecular isoform of human chorionic gonadotropin.

In an embodiment of this invention, the antibody specifically binds to a region of the early pregnancy associated molecular isoform of human chorionic gonadotropin comprising a carbohydrate moiety. According to one embodiment of this invention, the monoclonal antibody is B152. In an embodiment of this invention, a hybridoma cell (ATCC Accession No. HB-12467) is provided capable of producing monoclonal antibody B152. Another embodiment of this invention is the early pregnancy associated molecular isoform of hCG recognized by the B152 monoclonal antibody.

Further, the present invention provides a method for detecting non-trophoblast malignancy in a sample comprising: (a) contacting a sample with an antibody which specifically binds to the early pregnancy associated molecular isoform of hCG under conditions permitting formation of a complex between the antibody and the early pregnancy associated molecular isoform of hCG; (b) contacting the sample with a second antibody which specifically binds to intact non-nicked hCG without substantially cross-reacting with said antibody under conditions permitting formation of a complex between the antibody and the early pregnancy associated molecular isoform of hCG; (c) measuring the amount of complexes formed, thereby determining the amount of the early pregnancy associated molecular isoform of hCG in the sample; and (d) comparing the amount of early pregnancy associated molecular isoform of hCG in the sample determined in step (b) with the amount of early pregnancy associated molecular isoform of hCG in the sample determined in step (c), wherein a positive detection of early pregnancy associated molecular isoform detected in step (b) and a relative absence of the early pregnancy associated molecular isoform of hCG detected in step (c) indicates the presence of non-trophoblast malignancy in the sample.

According to an embodiment of this invention, the antibody is B152 or B109. In an embodiment of this invention, the detection antibody is B207 for B152 assay, B108 for B109 assay. In an embodiment of this invention, the non-trophoblast malignancy is ovarian malignancy or prostate malignancy.

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

In an embodiment, the present invention provides a method for detecting gestational trophoblast disease in a sample from a subject comprising (a) contacting a sample with an antibody which specifically binds to the early pregnancy associated molecular isoform of hCG under conditions permitting formation of a complex between the antibody and the early pregnancy associated molecular isoform of hCG; (b) contacting the sample with a second antibody which specifically binds to intact non-nicked hCG without substantially cross-reacting with said antibody under conditions permitting formation of a complex between the antibody and the early pregnancy associated molecular isoform of hCG; (c) measuring the amount of complexes formed, thereby determining the amount of the early pregnancy associated molecular isoform of hCG in the sample due to binding with the first antibody, and late pregnancy associated molecular isoform of hCG in the sample due to binding with the second antibody; (d) determining the ratio of early pregnancy associated molecular isoform of hCG to late pregnancy associated molecular isoform of hCG in the subject; and (e) comparing the ratio of early pregnancy associated molecular isoform of hCG to late pregnancy associated molecular isoform of hCG in the sample determined in step (c) over time, wherein a continuing high ratio of early pregnancy associated molecular isoform of hCG to late pregnancy associated molecular isoform of hCG in the sample determined in step (c) indicates the presence of gestational trophoblast disease in the subject.

In an embodiment of this invention, the antibody is B152 or B109. In another embodiment of this invention, the second antibody is B108 for B109 B207 for B152 assay. In an embodiment of the present invention, the gestational trophoblast disease is choriocarcinoma or hydatidiform mole.

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope $I^{125}$.

As described herein below, unexpected isoforms of hCG are produced during normal early pregnancy. Using an in vitro bioassay, it appears that these isoforms have enhanced potency for signal transduction. These isoforms can be measured using the novel sensitive, immunoassay described herein. This can help predict pregnancy outcome where one cause of early pregnancy loss is failure to produce the isoform of hCG of higher potency produced by successful pregnancies. This enables physicians to intervene to sustain a failing pregnancy. Identification of the nature of the hCG isoform required might provide the proper reagent needed to sustain pregnancy.

New antibodies for measurement of nicked forms of hCG described herein below were developed based on the hypothesis that forms of hCG, which have greatly reduced bioactivity, contribute to early pregnancy loss (EPL), due at least in part to diminished biopotency. Evidence was found that the hCG that appears in EPL patients displays reduced biological activity. However, it was determined that the cause of the reduced bioactivity is not the presence of nicked hCG in EPL patients. Instead, the hypothesis is that patients that carry pregnancies forward produce an isoform of hCG with enhanced bioactivity. The instant invention describes a unique immunochemical assay to measure this unexpected and previously uncharacterized isoform of early pregnancy hCG directly in clinical samples of blood and urine. One of the antibodies developed reacted against a nicked form of hCG isolated from a choriocarcinoma patient, was not specific for a nicked form of hCG but appeared to discriminate among carbohydrate variants of hCG. This antibody, designated B152, appears to preferentially bind hCG forms from choriocarcinoma patients. In studying the content of hCG isoforms during pregnancy, the unique and unexpected observation was made that B152 in the first four weeks of pregnancy measured much higher quantities of an isoform of hCG as compared to the standard hCG isoforms measured by the usual heterodimeric hCG assays exemplified by a previously described B109 based assay. In fact, in early pregnancy (days 9, 10, 11 postovulation) B152 measured as much as 20-fold more hCG, than did another monoclonal antibody, B109. Later in pregnancy, the B152 isoform declines and is lower in third trimester pregnancy urine than the standard isoforms measured by B109. A further striking observation was that in very early pregnancy, a high B152/B109 ratio correlates with a successful pregnancy outcome while a low ratio correlated with pregnancy loss. This discovery is important as the potentially overlooked isoforms of hCG described herein during pregnancy may be predictors of successful pregnancy outcome. Such an assay has wide medical applications and provides a clinician with opportunity to intervene very early in pregnancy if the assay indicated that the pregnancy appeared troubled.

An antibody, designated B152, produced by the hybridoma cell accorded ATCC Accession number HB-12467, generated against a nicked form of hCG isolated from a choriocarcinoma patient, but not specific for nicked isoform hCG is able to discriminate among carbohydrate variants of hCG. B152 is specific for an early pregnancy associated molecular isoform of hCG, which in the first four weeks of pregnancy is measured at much higher quantities than the hCG standard isoforms measured by the usual heterodimeric hCG assays exemplified by a previously described B109 based assay. Later in pregnancy, the B152 isoform declines and is lower in third trimester pregnancy urine than the standard isoforms measured by B109.

The hybridoma cell line B152 was deposited pursuant to, and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209 on Feb. 3, 1998 under ATCC Designation No. HB-12467. Likewise, the hybridoma cell lines producing the antibodies B207, B108 and B109 were also deposited pursuant to, and in satisfaction of, the requirements of the Budapest Treaty with the ATCC on Apr. 4, 2000 under ATCC Designation Nos. PTA-1626, PTA1625 and PTA-1624, respectively. All restrictions upon pubic access to these deposits shall be removed upon grant of a patent on this application and the deposits shall be replaced if viable samples cannot be made by the depository named hereinabove.

Briefly, three urine specimens per cycle, corresponding to days 9, 10, 11, post calculated day of ovulation were collected and analyzed in a screening assay (the "combo") which simultaneously detects intact, non-nicked hCG, hCG free beta subunit, and hCG beta core fragment. Individual determinations for each of these analytes, as well as for nicked hCG, and the form of intact hCG detected by monoclonal antibody B152 (EPMI hCG) were performed on these specimens. In addition, since the concentration of luteal phase hLH urinary analytes is a concern because of cross-reaction in hCG assays, levels of intact hLH, hLH free beta subunit and hLH beta core fragment were determined in the normal pregnancy cycles and the nonconceptive cycles. Table 1 summarizes the characteristics of immunometric assays employed.

This invention is illustrated in the Experimental Details section which follows. These sections are set forth to aid in an understanding of the invention but are not intended to, and should not be construed to, limit in any way the invention as set forth in the claims which follow thereafter.

The hybridoma cell line B152 was deposited pursuant to and in satisfaction of the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209 on Feb. 3, 1998 under ATCC Designation No. HB12467. The hybridoma cell lines producing the antibodies B207, B108, and B109 were also deposited with the ATCC pursuant to and in satisfaction of the requirements of the Budapest Treaty, on Apr. 4, 2000 under ATCC Designation Nos. PTA-1626, PTA-1625, and PTA-1624, respectively.

All restrictions upon availability to the public will be irrevocably removed upon granting of this patent and the deposit will be replaced if it should ever become enviable.

EXPERIMENTAL DETAILS FOR THE FIRST SERIES OF EXPERIMENTS

Example 1

Antibodies to and Analysis of Molecular Isoforms of hCG in Early Pregnancy and Early Pregnancy Loss Introduction Almost all investigations of the incidence of early pregnancy loss (EPL), either in normal populations or in populations at risk as a consequence of exposure to putative reproductive toxins (Hakim, R. B., et al., 1995; Lasley, B. L., et al., 1995) use assays for heterodimeric, non-nicked hCG or combination assays which include free beta subunit and beta core fragment of hCG. One concern about the forms of hCG to include in the measurement in EPL was heightened with respect to the nicking phenomenon described above. Because nicked hCG molecules are not measured by the antibodies employed in most EPL studies, the incidence of EPL is presumably underestimated by an amount proportional to the extent of nicking in the urinary molecule. Another concern of significant importance was a determination of the nature of the "hCG like" immunoreactivity in the urine in the periovulatory surge of the menstrual cycle (O'Connor J., et al., 1995). Recent reports have confirmed the existence of and documented the structure of a sulfated form of hCG produced in the pituitary (Birken, S., et al., 1996b). There is a pulsatile secretion of hCG in both men and non-pregnant women. (Odell, W. D.; Griffin, J., 1989 and Odell, W. D.; Griffin, J., 1987). The presence of a non-pregnancy associated form of sulfated hCG of pituitary origin, peaking at ovulation and perhaps persisting into the luteal phase, could potentially interfere with the accurate estimation of EPL.

Unappreciated isoforms of hCG in blood and urine very early in pregnancy may be more potent in vivo than the forms of hCG produced later in pregnancy. The absence of such isoforms may be one cause of early pregnancy loss. A sensitive and specific immunoassay system was designed and made to measure unique early pregnancy associated molecular isoforms (EPMI) of hCG. These isoforms, likely to differ by carbohydrate composition, are predictive of a successful pregnancy outcome. When these early pregnancy associated molecular isoforms of hCG are absent or present in low concentration, the pregnancy may be lost very early and be observed as only a "chemical" pregnancy. These hCG isoforms may resemble the forms of hCG produced in some choriocarcinoma patients from which the immunogen used to produce monoclonal antibody B152 was derived as described herein below. The isoforms resemble those from trophoblastic disease not in terms of nicking or intact peptide chains but likely in carbohydrate content. The present invention describes that the molar ratio of B152 to B109 epitopes are predictive of a successful pregnancy or a loss. Three categories of pregnant patients were analyzed: (a) normal pregnant women, (b) women who experience recurrent abortions, (c) women undergoing embryo implantation.

It is possible to determine the hCG isoforms present in the blood and urine of women who have a history of recurrent spontaneous abortion and a similar analysis of women undergoing embryo implantation. The combined EPL and spontaneous abortion rate in healthy populations is 31%. Subjects who experience three consecutive recurrent spontaneous abortions have a 32% risk of sustaining another (Hill, J. A.; Anderson, D. J., 1990). In in vitro fertilization IVF pregnancy, the loss rate is 70% with non-donor sperm and 50% when donor sperm is used. Delineation of pregnancies with a negative outcome from pregnancies with a positive outcome can be based on differences in the concentrations of EPMI hCG isoforms (i.e. as differences in the B152/B109 ratio in patients). In addition, specimens from gestational trophoblastic disease (GTD) can be used to discriminate between GTD and normal pregnancy.

Results

In Vitro Bioassay For hLH/hCG

An hCG bioassay was constructed employing CHO cells expressing functional human LH/CG receptor. Table 1 illustrates the differences in vitro in biological activity between nicked and non-nicked hCG as measured by this assay. This system, h s been used to evaluate the activity of pituitary and placental hCG (Birken, S., et al., 1996b). Preparations of hCG were tested for nicked and non-nicked molecular isoforms of hCG in a second recombinant bioassay system (Ho, H-H., et al., 1997). Similar results were obtained in both systems.

Normal Pregnancy Values Compared With EPL Values.

Results indicated that nicked hCG is not a significant molar constituent of either early pregnancy or EPL. Data indicated that biological activity is not correlated with nicked hCG, but is instead ascribed to a form of hCG recognized by the B152 monoclonal antibody ATCC # HB-12467 an early pregnancy associated molecular isoform of hCG (EPMI hCG). It has been established that there is diminished hCG bioactivity associated with EPL as compared to early normal pregnancy (Ho, H-H., et al., 1997). Thus, diminished hCG biological activity is a factor in EPL as a consequence of a heretofore unappreciated isoform of hCG—an early pregnancy associated molecular isoform of hCG.

hCG Urinary Analytes. Metabolites of hCG and hLH were studied in a variety of states (Birken, S., et al., 1996a). One study indicated a 31% pregnancy loss (Zinaman, M J, et al., 1996) while another indicated a 17.4% rate of early pregnancy loss based on hCG assays (Ellish, N. J., et al., 1996). It is known that hCG and hCG beta core can be readily transferred from the uterus to the circulation even in the absence of implantation (Charg, P. L., 1997). The molecular spectrum of hCG urinary analytes in EPL cycles, normal conceptive cycles and non-conceptive cycles have been evaluated. The study design and demographics of the investigation have been described (Ellish, N. J., et al., 1996).

Briefly, three urine specimens per cycle, corresponding to days 9, 10, 11, post calculated day of ovulation were collected and analyzed in a screening assay (the "combo") which simultaneously detects intact, non-nicked hCG, hCG free beta subunit, and hCG beta core fragment. Individual determinations for each of these analytes, as well as for nicked hCG, and the form of intact hCG detected by monoclonal antibody B152 (EPMI hCG) were performed on these specimens. In addition, since the concentration of luteal phase hLH urinary analytes is a concern because of cross-reaction in hCG assays, levels of intact hLH, hLH free beta subunit and hLH beta core fragment were determined in the normal pregnancy cycles and the non-conceptive cycles. Table 15 summarizes the characteristics of immunometric assays employed.

TABLE 1

Assay format and specificity

| Assay format | Primary analyte | % cross-reactivity with related analytes |
|---|---|---|
| B109-B108* | intact non-nicked hCG | <1%[b] |
| B201-C104* | hCG free beta subunit (non-nicked + nicked) | 1% hCG; 10% hCG nicked (pregnancy); <1%[b] |
| B210-B108* | hCG beta core fragment | 2% hLH beta core fragment; <1%[b] |
| B151-B207* | hCG nicked | 10% hCG nicked free beta subunit; 12% hCG non-nicked; 2% hCG free beta subunit; 2% hLH; 5% hLH free beta subunit; <1%[b] |
| B152-B207* | choriocarcinoma hCG (C5) and choriocarcinoma hCG free beta subunit | 100% hCG nicked (C5); 190% hCG free beta nicked (from C5); 10% hCG nicked (pregnancy); 5% hCG free beta nicked (pregnancy); 7% hCG (pregnancy); 6% hCG free beta subunit; <1%[b] |
| B406-A201* | hLH | <1%[a] |
| B505-B503* | hLH beta core fragment | <1%[a] |
| B408-B409* | hLH free beta subunit | 29% hLH; <1%[a] |

[a](if not indicated) hLH, free beta hLH, hLH beta core fragment, hCG, free beta hCG, hCG beta core fragment;
[b](if not indicated) the same as [(a)] plus nicked hCG and nicked free beta hCG (pregnancy).

The results indicate that nicked hCG does not constitute a significant mole fraction of urinary hCG immunoreactivity in either EPL or early normal pregnancy. In addition, there is a substantial excretion of hCG free beta subunit in some subjects in both pregnancy and EPL. Further, both EPL and normal pregnancy cycles variably express all of the measured analytes. Although both the incidence and level of expression are different between EPL's and normal pregnancy, there is no hCG related analyte unique to either state. There was, however, a clear difference between the hLH associated analytes in the control population (non-conceptive cycles) and the normal pregnancy group. Virtually all of the non-pregnancy cycles expressed hLH free beta subunit and hLH beta core fragment while only a third of the conceptive cycles had detectable levels of either analyte. Intact hLH proved to be a minor constituent of the hLH profile in both groups.

These findings demonstrate both the necessity of measuring hCG beta core fragment in the detection of EPL, and also of making sure that the hCG beta core assay does not cross-react with beta core hLH, which is demonstrated to be present in that part of the luteal phase where EPL measurements are performed. The data is summarized in FIG. 2.

Statistical analysis was performed after transformation of analyte values to mole fractions so as to produce a more useful analysis due to the wide excursion of hCG analyte values among groups. The mole fraction data were evaluated by discriminant analysis and by a mixed effects model incorporating LMP (last menstrual period date) The discriminant analysis was performed both with and without "outliers" (defined as values greater than two standard deviation from the mean) removed. Both approaches produced similar results.

A quadratic discriminant analysis based on a cross-validation method in order to minimize bias correctly classified 91% of the normal pregnancy subjects and 80% of the EPL subjects.

The mixed effects analysis, testing for interactions between mole fraction of analyte and time since LMP found no significant time or group (EPL vs. normal) effects in the intact hCG assay. In the free beta subunit of hCG assay, there is a significant group effect but no time trend. In both the hCG beta core fragment measurement and the B152 measurement, both the hormone levels and the time trend from LMP were significantly different between the EPL and pregnancy groups. This study produced several important findings. It defined the spectrum of analytes which in both early pregnancy and EPL, thereby resolving the issue of which hCG analytes to measure in epidemiological studies in which EPL is the end point determination. More importantly, it illustrated for the first time that there are significant differences both in the pattern of analytes and the time course of their appearance between early normal pregnancy and EPL. This observation facilitates very early prediction of a distressed pregnancy by urinary hCG measurements at a time which would permit therapeutic intervention.

Immunoreactivity of Different Forms of hCG in the Two IRMA's (B152-B207 and B109-B108)

Figure 3A:
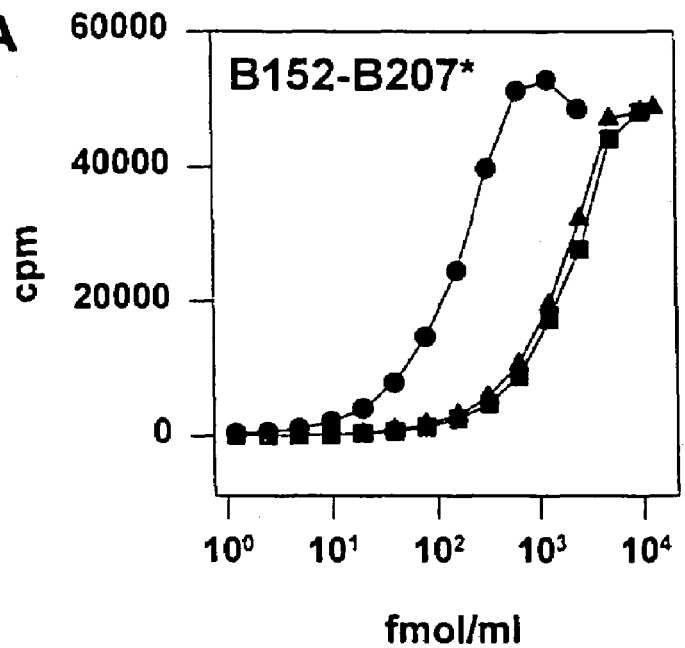
Figure 3B:
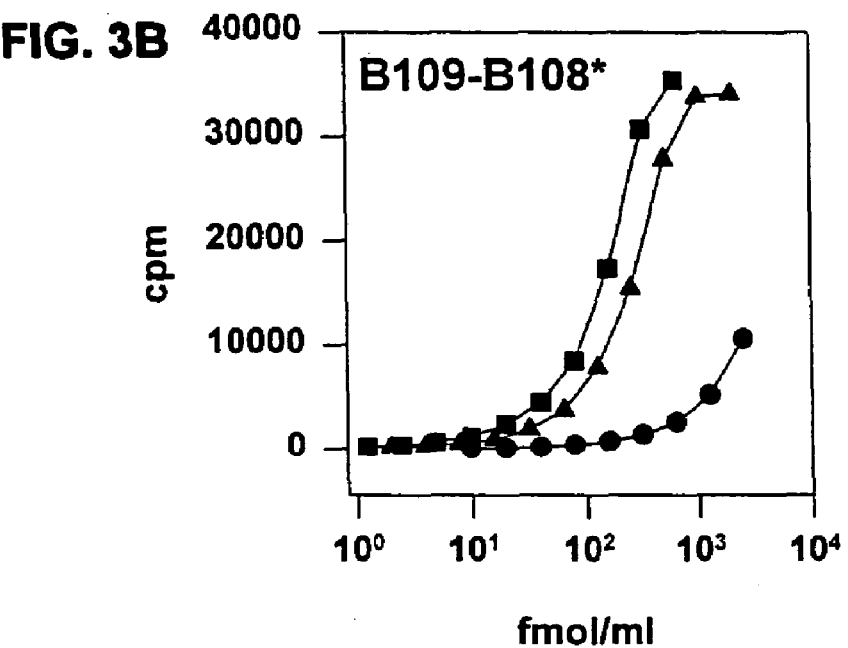

The relative binding of three different forms of hCG (urinary hCG, pituitary hCG and choriocarcinoma hCG C5) has been characterized in the two hCG assays (FIG. 3). Urinary non-nicked hCG and pituitary hCG are recognized nearly equally well by the two IRMASs, while C5 recognition is quite different. The B152-B207* assay is more sensitive to C5, which is to be expected because B152 antibody was developed and selected on the basis of higher affinity to C5. Urinary non-nicked hCG is purified from the CR127 preparation of pooled normal pregnancy hCG. Conversely C5 is recognized with lower affinity by the B109-B108* assay, which has primary specificity for the hCG isoforms of later pregnancy.

We have developed a method to directly profile changes of hCG isoforms in serum or urine throughout pregnancy. Two IRMAs for hCG are employed, each based on monoclonal antibodies to different hCG epitopes. The B109-B108* assay is a commonly used intact hCG assay to the heterodimeric-dependent epitope. A new assay, B152-

B207*, is most likely sensitive to the carbohydrate portion of hCG carboxyterminal peptide. The same standard non-nicked hCG was used in both assays. Non-nicked hCG was employed since the B109 assay reacts poorly with nicked forms of hCG while the B152 assay does not discriminate between nicked and non-nicked forms of the hormone. The B152 assay detected with greatly enhanced sensitivity hCG isoforms which appear earlier in pregnancy than isoforms measured by the B109 assay (O'Connor et al. 1998). Prior to development of the new immunometric assay system described in this report, it was not possible to readily discern the changes in hCG isoforms from very early pregnancy to mid pregnancy. The only available procedure for examining these changes was isoelectric focusing of every patient specimen followed by immunoassay of every focused fraction (Berger et al. 1993; Ulloa-Aguirre et al. 1990). The IEF pattern reflects the heterogeneity of the charged sugar, sialic acid which varies with the multi-antennary structures of the carbohydrate moieties in which sialic acid is the terminal sugar. Although we do not yet know the precise nature of the isoform epitopes being measured, the evidence for carbohydrate discrimination is based upon the hyperglycosylated structure of the immunogen, C5, used to develop the B152 monoclonal antibody and the antibody's reactivity with the hCG isoforms found in the JAR choriocarcinoma cell line. C5 hCG was isolated from a choriocarcinoma patient and has been thoroughly characterized as to its protein and carbohydrate content and structure (Elliott et al. 1997). It has been shown that C5 (and hCG from other choriocarcinoma subjects) differ in the protein moiety mainly by the presence of an increased number of nicked sites and by increased glycosylation relative to the hCG of normal pregnancy. In comparison with the hCG of normal pregnancy, choriocarcinoma derived hCG has increased fucosylation of the N-linked biantennary oligosaccharides in the beta subunit. In addition, the O-linked oligosaccharides in preparation C5 (a form of hCG produced from a single patient with choriocarcinoma) has a 100% tetrasaccharide core on the COOH-terminal region of the beta subunit. Normal mid pregnancy hCG has only 10-20% of this structure (Elliott et al. 1997). These observations, plus our own determination that the hCG synthesized by the JAR choriocarcinoma cell line provides a B152/B109 isoform ratio similar to that observed in early pregnancy, leads us to the conclusion that in very early pregnancy, the developing trophoblast secretes an isoform of hCG which resembles that produced in choriocarcinoma.

We have also tested recognition of pituitary hCG since its N-Asn carbohydrates differ somewhat from those of placental hCG, bearing a closer resemblance to those of hLH which have both sialic acid and sulfate groups (Birken et al. 1996. The carbohydrate structure of the b COOH-terminal portion of pituitary hCG is not yet known. Since B152 did not recognize any substantial differences between pituitary and placental hCG (FIG. 3), differences in N-Asn recognition are unlikely. In terms of the COOH-terminal carbohydrates, it appears that pituitary and placental hCG (mid-pregnancy isoforms) may be similar, assuming the O-linked carbohydrate on the C5 antigen is part of the epitope of B152.

Example 2

B152/B109 Ratio Predicts Pregnancy Outcome

The B152/B109 Ratio Measured In Urine Samples Throughout the Pregnancy

Figure 4:
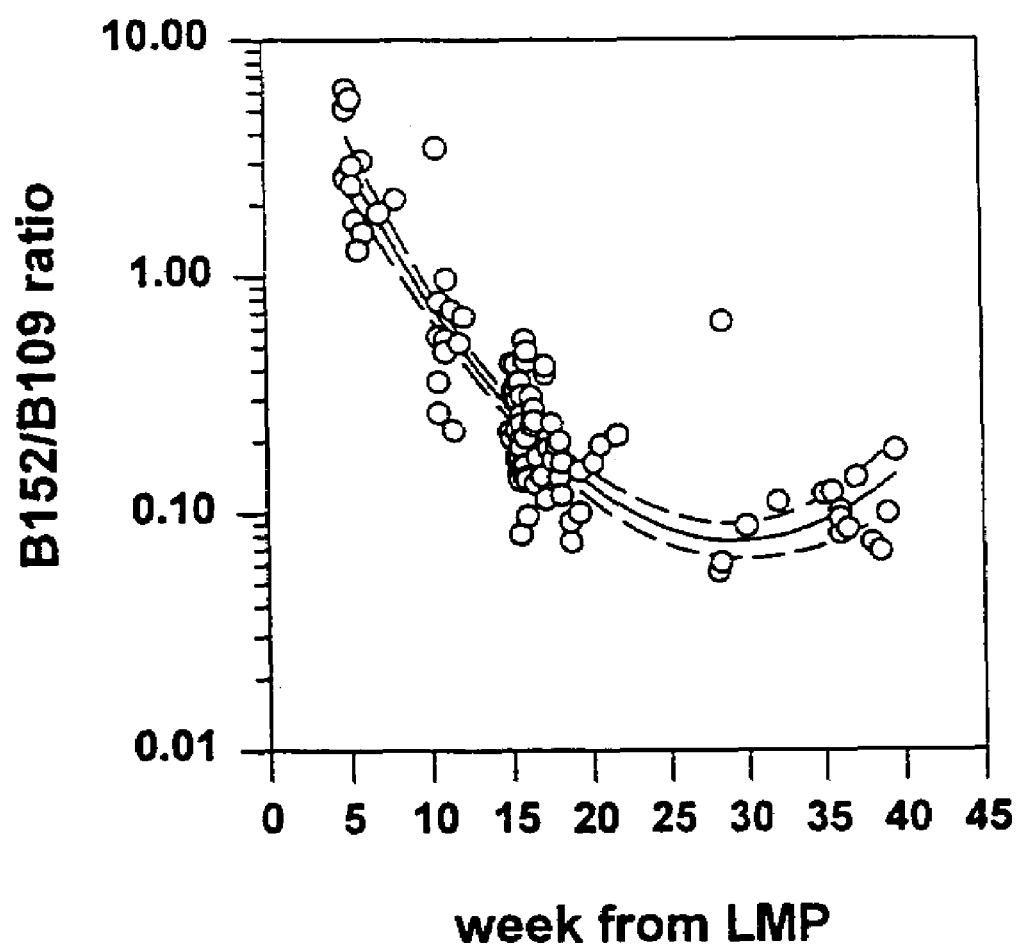

The relative concentrations of hCG isoforms in 103 normal pregnancy urine samples (5-39 weeks post last menstrual period—LMP) were determined by two immunometric assays (B152-B207* and B109-B108*). Both because of the wide range of hCG concentrations in different samples, even at the same gestational age, and because neither of the assays is totally specific for the two (or more) families of hCG isoforms present, we find that presenting the data as a ratio of the observed two isoform groups more clearly delineates the change in isoform content as pregnancy progresses. This calculated ratio is shown in FIG. 4. In weeks 5-8 of pregnancy, the ratio of B152/B109 isoforms ranged between 6.2 and 1.3, indicating a predominance of the B152 isoform(s) in early pregnancy. During the 10 to 12 week period, the ratio ranged from 1-0.2, indicating that an inversion in hCG isoform content is occurring as pregnancy progresses. This decline in the ratio continues, ranging from 0.54-0.08 in the 15-18 week period and reaching an inflection point at 29 weeks. At that time, the ratio reached a value of around 0.06 after which the ratio displayed a rise to a range of 0.2-0.07 in the 37-39.5 weeks of gestation time period.

Statistical analysis involved fitting the log transformed ratio data to second and third order polynomial regression models. Since the third order term was not significant (likelihood ratio $c^2(1)=1.32$, P=0.25), the second order model was used ($r^2=0.793$). The log B152/B109 ratio reached an inflection point at LMP=29 weeks, based on this model.

The B152-B207* values reflect a measurement of the B152 isoform in terms of later pregnancy hCG equivalents, not in absolute quantities. It must be emphasized that the "absolute" concentrations measure in the B152 assay cannot be compared with the results of the B109 assay on an equimolar basis since the potency of the hyperglycosylated isoform is much higher in the B152 assay vis-à-vis the standard, i.e. normal later first trimester pregnancy hCG. The actual molar values of this isoform are on the order of tenfold less than those recorded in the assay. For this reason we have chosen not to analyze absolute molar quantities of the two analytes but only the ratio of the two measurements.

Even in normal pregnancy, the hCG values obtained vary widely according to the characteristics of the immunological reagents employed (Cole and Kardana, 1992; Cole et al. 1993). We hypothesize that the two assays described in this report primarily detect hCG isoforms at opposing ends of this spectrum, each primarily recognizing a subset of closely related molecules in the continuum of early to later pregnancy hCG molecular forms.

We have retained the use of normal pregnancy hCG as the standard in B152-B207* assay, despite its decreased affinity in this antibody configuration. The reasons for this include the limited and unrenewable supply of C5 (which was isolated from the urine of a single patient) and the variability in data which would result from investigations using different standards. The consequences of this choice are that the early pregnancy hCG isoforms have markedly increased immunopotency over that of normal pregnancy and hence their molar quantities are overestimated in this assay. We use this difference in affinity to our advantage by employing a ratio of the molar results of two assays (B152 and B109). Either assay taken alone obscures his change due to the wide excursion of hCG values which occur in normal pregnancy.

Others have documented progressive changes in hCG isoforms throughout pregnancy. Skarulis et al. found that the fucose content of both intact hCG and also its free beta subunit increased as pregnancy progressed (Skarulis et al. 1992). Diaz-Cueto et al. investigating the isoelectric focusing pattern of circulating hCG throughout pregnancy, found that in early pregnancy, more than 80% of the hCG isoforms were acidic. This fraction decreased to less than half (47%) late in the third trimester (Diaz-Cueto et al. 1996). In contrast, Wide and Hobson found that the hCG of early pregnancy was more "choriocarcinoma-like" by virtue of its greater biological activity than the hCG of normal pregnancy (Wide and Hobson, 1987). Fein et al., in a study which employed gel filtration determined that first trimester hCG was a larger size than that of the third trimester. Treatment with exoglycosidases eliminated the size differential, indicating that the first trimester hCG was more highly glycosylated (Fein et al. 1980).

The B152/B109 Ratio In Matched Serum/Urine Samples In the First and Third Trimesters of Pregnancy Compared with hCG From JAR Cells.

Figure 5:
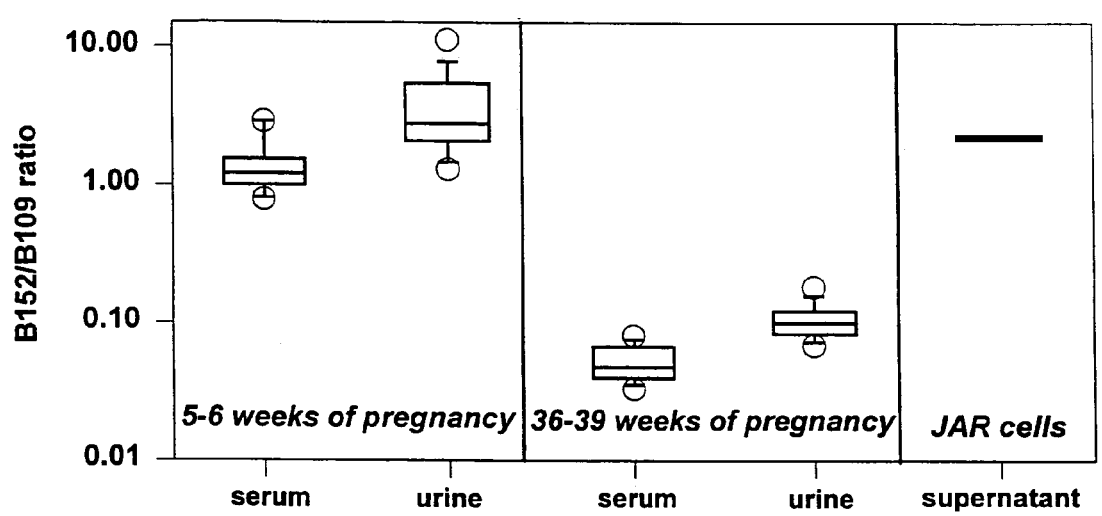

The B152/B109 ratio in serum is analogous to that found in matched urine samples and undergoes a similar change as pregnancy progresses (FIG. 5). The B152/B109 ratio in the cell supernatant from JAR cells (a choriocarcinoma derived cell line) was similar to that of early pregnancy.

The B152/B109 ratios of both serum and urine hCG concentrations are significantly higher in the first trimester as compared to the third trimester of normal pregnancies (Table 2). Significant differences between serum and urine hCG concentration ratios as well as log transformed ratios in early (5-6 weeks) and late (36-39 weeks) gestation were evaluated by paired. t-tests (Table 3). In both the first and third trimesters, urinary B152/B109 ratios were significantly higher than serum ratios, indicating that there was a preferential clearance of the B152-recognized isoform into urine, regardless of the relative concentrations of the two isoforms.

TABLE 2

Analysis of the B152/B109 ratio in serum and in urine in the first vs third trimesters of pregnancy.

| Measure | T-test(df) | P |
| --- | --- | --- |
| Serum, ratio B152/B109 | t(11) = 6.65 | 0.0001 |
| Serum, log(ratioB152/B109) | t(23) = 21.61 | 0.0000 |
| Urine, ratio B152/B109 | t(11) = 4.64 | 0.0007 |
| Urine, log(ratioB152/B109) | t(15.7) = 16.85 | 0.0001 |

TABLE 3

Analysis of the B152/B109 ratio in serum vs urine in the first and third trimesters of pregnancy.

| Gestational age | Measure | Paired-t (df) | P |
| --- | --- | --- | --- |
| 5-6 weeks | Ratio B152/B109 | t(11) = 3.25 | 0.0077 |
|  | Log(ratioB152/B109) | t(11) = 6.25 | 0.0001 |
| 36-39 weeks | Ratio B152/B109 | t(10) = 5.47 | 0.0003 |
|  | Log(ratioB152/B109) | t(10) = 7.14 | 0.0001 |

The B152/B109 Ratio In Urine Samples From IVF Patients

In urine samples from IVF patients (1-4 weeks post embryo transfer—ET) the B152/B109 ratio was again between 2-8 and decreased as pregnancy progressed (FIG. 6), similar to that observed in natural conceptions. The effect of pregnancy duration with respect to outcome variables could best be represented by a linear or quadratic function. ANCOVA models including the second order week were fitted to the general equation: Outcome=(effect of time post ET)+(effect of diagnosis). After an appropriate ANCOVA model was determined, the least square means (adjusted for week post ET effect) were compared among the normal pregnancy, ectopic pregnancy and spontaneous abortion populations (Table 4). The log transformed values of both B109-B108* and B152-B207* measured hCG forms discriminated both ectopic pregnancy and spontaneous abortions from normal pregnancy (P=0.0001). The ratio of the log transformed values discriminated abortion from normal pregnancy (P=0.016). However, neither the ratio of B152/B109 nor the log of that ratio discriminated either of the pregnancy disorders from normal pregnancy.

A significant number of spontaneous abortions and ectopic pregnancies occur in IVF pregnancies. We did not find a difference in the ratio of the isoforms between either of these two categories as compared to normal controls, possibly a consequence of low statistical power. However a significant difference was found between the B152 hCG isoforms levels in normal pregnancy and spontaneous abortion. This supports our previous finding in early pregnancy loss, where diminished or absent levels of the B152 isoforms characterized an early pregnancy loss (O'Connor et al. 1998).

TABLE 4

IVF patients: analysis of covariance of hCG isoforms among normal pregnancy (np), ectopic pregnancy and spontaneous abortion as a function of gestational age.

| Outcome | [c]Adjusted $R^2$ | [e]-F | P | [d]-Pairwise Difference |
| --- | --- | --- | --- | --- |
| [a]Log (ratio B152/B109) | 0.51 | 0.89 | 0.41 | none |
| [a]Log (B109-B108*) | 0.56 | 21.33 | 0.0001 | np vs abortion & ectopic |
| [b]Log (B152)/log (B109) | 0.45 | 4.34 | 0.016 | np vs abortion |
| [b]Log (B152-B207*) | 0.50 | 26.94 | 0.0001 | np vs abortion & ectopic |

[a]ANCOVA model with 2nd order polynomial coefficient (or parameter).
[b]ANCOVA model with only 1st order (linear) coefficient.
[c]Adjusted $R^2$ is a $R^2$ adjusting number of coefficients on the ANCOVA model so that comparisons of two $R^2$ with different ANOVA models with different number of coefficients are meaningful.
[d]-"Pairwise difference" is based on t-test comparing the least-square means of outcome variables (after adjusting effect of week ET).
[e]-Degree of freedom (df1, df2) for F-test are (2, 82) for a model with only linear coefficient and (2, 81) for a model with both linear and 2nd order coefficient.

HCG Analysis Of Trophoblastic Disease Samples

Trophoblast disease serum (17 samples) and urine (28 samples) were obtained from patients post therapy and hence contained low hCG levels. Due to limited amounts of sample all of these specimens were run at a 1:10 initial dilutions. HCG levels in serum were low. The highest hCG concentration in serum was 202 fmol/ml in the B152-B207* assay, with a corresponding value of 148 fmol/ml in the B109-B108* determination. Six of seventeen samples in serum had detectable levels, with 4/6 having a higher value in the B152-B207* assay. Of the 15/28 positive urine samples however, 14/15 had higher levels in the B152-B207* assay than in the B109-B108* assay, with the highest hCG value being 20000 fmol/ml in the B152-B207* assay and 18715 fmol/ml in the corresponding B109-B108* assay. Due to the small sample size, no statistical treatment was performed on this data, but even in these post-treatment patients the B152/B109 ratio was $\geq 1$, which corresponds to the early pregnancy hCG isoform ratio.

The specimen limitations discussed above precludes our reaching any definitive conclusion on the analysis of trophoblastic disease samples. However it appears as might be anticipated that the B152 assay is more sensitive than B109 assay in detecting hCG immunoreactivity in the blood and in the urine of trophoblastic disease patients, even after treatment.

Chromatography Of First Week of Gestation Pregnancy Pool

In order to determine whether the B152-B207* assay recognized other forms of hCG associated immunoreactivity in addition to the intact hCG molecule, specimens were pooled. FPLC on tandem SUPEROSE 12 columns followed by immunoassay of the fractions for all of the characterized forms of hCG revealed that only the intact hCG molecule (or hCG free beta subunit) gave a signal in this assay (See FIG. 8). There were no lower molecule weight fragments identified by the B152-B207* assay. The hCG free beta analyte was measured in the 159 urines described in FIG. 6 and was found to make a negligible contribution to overall hCG immunoreactivity in these specimens.

Molecules Recognized By Monoclonal Antibody B152 In Urine and Pituitary Extracts. In order to define the nature of the hCG isoforms recognized by B152, high resolution gel filtration columns of both pituitary extracts and postmenopausal urine concentrates were used (See FIG. 8). The rationale for use of pituitary extracts is to determine cross-reactive molecules, specifically those which are glycosylated, which are plentiful in pituitary which contains the entire family of glycoprotein hormones, hLH, hTSH, and hFSH as well as free subunits and the pituitary form of hCG. Two peaks are detected in both of these cases. Only one peak was detected in similar studies of pregnancy urine concentrates as described earlier. In the pituitary, it is likely that the larger molecule is pituitary hCG (70 K) while the smaller sized molecule is hLH. Since hLH is present at 100× or so as compared to pituitary hCG, the apparent similar concentration of immunoreactivity indicates that B152 has reduced cross-reactivity to hLH as compared to hCG. Likewise, both hCG and hLH occur in postmenopausal urine, again with much more hLH than hCG and the B152 pattern is similar to that of the pituitary extract. These results show that B152 is generally hCG specific except for cross reactivity to hLH (as shown by standard cross-reaction studies in Table I) and that its carbohydrate specificity is both to the protein portion as well as to the carbohydrate moieties of hCG (and to a lesser extent of hLH) since it does not react with the multitude of other glycoyslated proteins present in the pituitary nor with those in postmenopausal urine except for hCG or hLH-related molecules.

Figure 1:
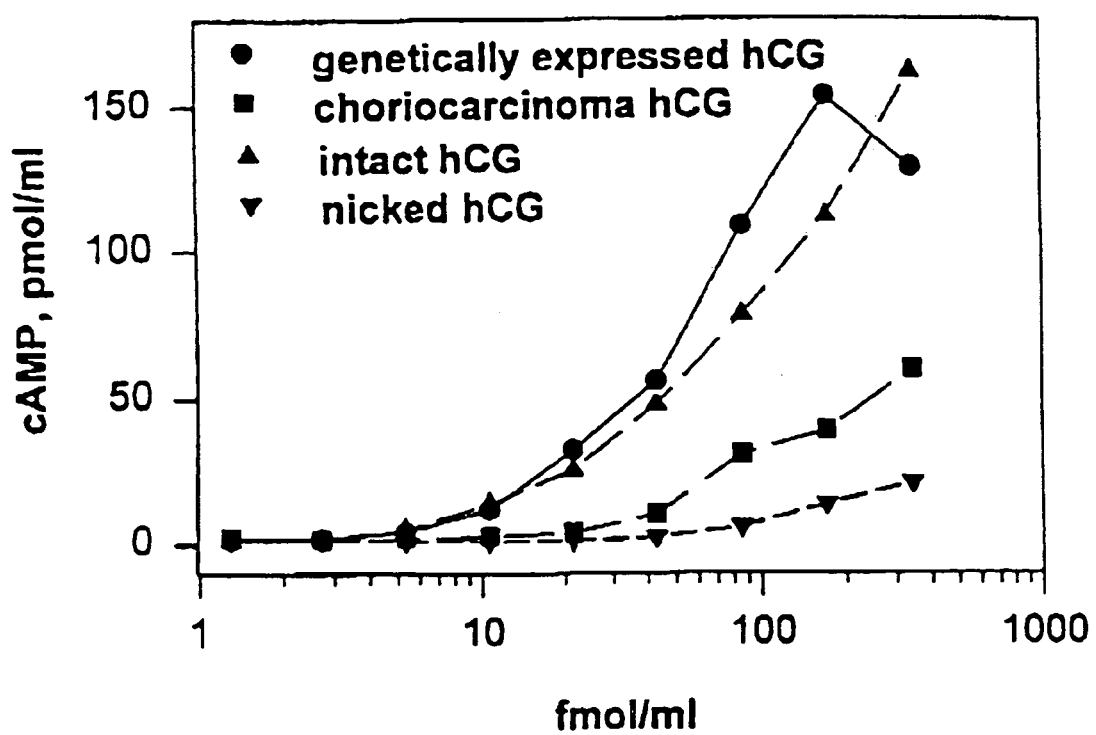
FIG. 1

Serum and urine specimens were analyzed using two assays, B109-B108* and B152-B207*, which recognize the difference in molecular isoforms of hCG. See Table I. The. in vitro bioassay for hLH/hCG is described above. (See FIG. 1). Results are indicated in FIGS. 6-11. The immunometric assay employs 96-well microtiter plate technology. The coating antibody, at a concentration determined to provide the most satisfactory combination of sensitivity and range, is applied to the microtiter wells (Immulon IV, Dynatech Laboratories) in carbonate buffer (0.2 M, pH 9.5). The plates are incubated with the coating solution at 4° C., overnight, then aspirated, washed with washing solution (0.05% Tween, 0.15 N NaCl), and blocked with a 1% solution of BSA (three hours at room temperature). The BSA solution is aspirated and the appropriate hCG standards (200 µl/well), in buffer B (PBS/0.1% bovine IgG/0.1% sodium azide), or in hCG free serum (Chemicon, Inc.), or hCG free urine, as appropriate to the specimen matrix, and specimens are added to the wells. The plates are sealed with plate sealers, and incubated overnight at 4° C. The controls, specimens, and standards are then aspirated, the plates washed 5 times with washing solution, and iodinated detection antibody in buffer B (200 uL/well, 100,000 cpm/well) added and incubated overnight at 4° C. The wells are again aspirated, washed 5 times with washing solution, separated and counted (Packard Cobra gamma counted). Values are interpolated from a smoothed spline transformation of the count data. This assay procedure, as well as assay validation has been previously reported (O'Connor, J. F., et al., 1988).

Creatinine analysis, when urine values are normalized to creatinine, is performed in a microtiter plate format following a modification of the Taussky procedure (Taussky, H. H., 1954).

Descriptive statistical and graphical methods are used to measures of serum and urine samples from normal healthy pregnancies to identify the distributions a) between patient first trimester average B152 levels, B109 levels and B152/B109 ratio; b) between patient variability in time to B152/B109 ratio reaching 1.00; and c) between patient variability in time to B152/B109 ratio declining by ⅓rd from first trimester maximum levels. The variability in the timing of the crossover in the ratio of these two analytes provides an empirical basis from which to estimate the value of these markers as biochemical signatures of a viable third trimester fetus.

Comparison of the assay profile of healthy normal pregnancies to those of unsuccessful pregnancies from failed IVF implantations, two non-parametric hypotheses are available: 1) the proportion of pregnancies in which the B152/B109 ratio falls below 1.00 is no different in healthy normal and unsuccessful IVF pregnancies; 2) the proportion of pregnancies in which the B152/B109 ratio declines by ⅓rd from first trimester maximum levels is no different in healthy normal and unsuccessful IVF pregnancies. These hypotheses can be tested as a difference between two proportions. For example, a comparison of week 14 vs. week 9, week 13 vs. week 6, week 12 vs. week 5 or week 11 vs. week 4 pregnancies to show a reversal of the B152/B109 ratio in healthy normal pregnancies and unsuccessful IVF implantations, respectively. The power analyses apply to an outcome defined as the time at which the B152/B109 ratio declines by ⅓rd from first trimester maximum levels, although this outcome would necessarily provide earlier detection of pregnancy failure than the reversal of the B152/B109 ratio. Patterns of results less discriminantly different from these indicate a rejection of the dichotomous outcome of B152/B109 ratio reversal as a clinically meaningful marker of pregnancy failure.

Alternatively, the same two non-parametric hypotheses can be recast as parametric hypotheses by considering the timing of the biochemical events within the assay profile of healthy normal pregnancies and unsuccessful pregnancies from failed IVF implantations: 1) the time at which the B152/B109 ratio falls below 1.00 is no different in healthy normal and unsuccessful IVF pregnancies; 2) the time at which the B152/B109 ratio declines by ⅓rd from first trimester maximum levels is no different in healthy normal and unsuccessful IVF pregnancies. Of course, the objective is to provide an empirical basis from which clinicians may counsel their patients. Thus, it is important to adopt a logistic model for this component of the data analysis. With pregnancy success as the outcome, logistic models allow the estimation of the (symmetrical) hypothesis of increase in risk of pregnancy failure for each additional week where either the B152/B109 ratio has failed to decline by one third from first trimester baseline maximum values or the B152/B109 ratio has failed to become less than 1.00 (measured in weeks). The logistic model enables specification of the time at which results indicate a particular pregnancy exceeds an a priori defined likelihood of failure, given assay data regularly available during pregnancy, and allows incorporation of other risks for pregnancy failure in the same data analytic framework to assess the relative contribution of threats to pregnancy loss. The Cox proportional hazard model may be used to examine predictors of the crossover rates. Mixed effects models can also analyze repeated measures of the B152/B109 ratios taken during entire cycles. These models are particularly useful since they allow inclusion of incomplete and imbalance data (i.e. data with missing values and unequal timing of data collection), to estimate effects of time-varying covariates, to model dependency structure of repeated measures and to model possible heterogeneity of the ratio measures within each experimental group.

B152 hCG isoforms isolated from early pregnancy urine and determination of their protein and carbohydrate structures. Using the already developed scheme of concentration and immunoaffinity extraction of urine, hCG molecules are isolated from urine collected from women in early pregnancy for both protein and carbohydrate analyses. According to one approach, molecules are isolated from HPLC fractions, digested with proteases before and after reduction of disulfide bonds, examination of the resultant peptides by mass spectrometry and/or sequence analysis, isolation of carbohydrate moieties after glycosidase digestions and determination of carbohydrate structures by a combination of specific glycosidases and retention times on specialized anion exchange columns as compared to know branch-chain oligosaccharide standards. In a similar approach, the final purification stage for the isolated hCG isoforms is SDS gel electrophoresis. Both protease digests and glycosidase digests are performed on the blotted and cutout band. This method results in greater purity of the protein and less artifactual errors due to contamination by carbohydrates which are not in the purified protein but are derived from outside contaminants.

carbohydrate compositional analyses and oligosaccharide branched chain identifications. The MALDI TOF mass spectrometric method may be used to confirm oligosaccharide structures by using specific glycosidases on the glycopeptides and determining the change in molecular weight as the sugars are digested off the glycopeptide. Only the hCG beta COOH peptide can be expected to contain O-linked sugar moieties. These are of special interest since it is thought that B152 has significant reaction with this region. The structures of this region can be determined in a similar fashion using enzymes that specifically release O-linked glycans. The O-linked structures has been previously examined using standard reference pregnancy hCG (Cole, L. A., et al., 1985). The O-linked branched chain structure are determined by a similar strategy using the Dionex chromatographic system as well as specific glycosidases on the C-terminal glycopeptides and Mass Spectrometry. In one study (Elliott, M. M., et al., 1997), these techniques were used to elucidate the carbohydrate structures of CR series hCG preparations (standard urinary pregnancy hCG) arid compared them to the structures of patient samples such as C5 which was the immunogen employed to generate antibody B152. It was found that C5 contained significantly more mono and tri-antennary (2× mono and 3× tri-structures than the CR preparations) on the N-Asn residues. It was also found that more tetrasaccharide structures were on the hCG COOH-terminal peptide O-Serine residues in the choriocarcinoma hCG isoform than in the CR preparations.

Biological activity and metabolic clearance of hCG isoforms. Biological activity is a function both of molecular structure and half-life in the circulation, which can be influenced by structure. Alterations in carbohydrate/sialic acid content of the glycoprotein hormones are thought to be responsible for the changes in hCG biological/immunological activity observed throughout pregnancy. In addition, signal transduction at the receptor is influenced by the pI of the hCG isoform and the presence or absence of carbohydrate. Thus, it is valuable to examine both receptor binding and biological activity in vitro and, in order to determine the mechanism of action, to distinguish receptor binding and signal transduction as well as relative potency of signal transduction along with in vivo bioactivity determinants such as circulating half life. Studies, including clearance rates, are performed on B152 hCG isoforms of early successful pregnancy, hCG from third trimester pregnancy, and the reference urinary hCG preparation, CR 127.

Example 3

B152 And B151 Immunoreactivity In Non-Trophoblastic Malignancy

With the exception of trophoblastic disease and testicular cancer, hCG is expressed in the blood of about 20% of patients with all other types of cancer(Hussa, R. O., 1987). HCG beta core fragment in the urine has a significantly higher level of expression, especially in gynecological malignancy. Since the B152 antibody was developed to a form of hCG produced in a malignancy, it was of interest to examine the expression of B152 and nicked hCG immunoreactivity (B151) in non-trophoblastic malignancy. Accordingly, blood and urine derived. from men undergoing chemotherapy for prostate cancer or women for ovarian cancer were evaluated for the expression of hCG isoforms in plasma and urine. It is significant that in prostate cancer, B152 hCG immunoreactivity is found in the blood and urine of prostate cancer patients in instances when there is no hCG detected by B109-B108*. In ovarian cancer patients evaluated, there is evidence of nicked hCG in the blood, even in the absence of both B109 and B152 immunoreactivity. Neither of the above groups demonstrated the presence of hCG immunoreactivity when the standard pregnancy derived hCG assay was employed. It is reassuring to find that nicked hCG, the existence of which has been documented by several investigators, can be found and reliably measured in a clinical setting.

Experimental Discussion

In the course of these studies, a potentially important new signal was observed in the urine of women early in pregnancy, namely an epitope of a form of hCG which may indicate the likely success of carrying a pregnancy. Likewise, absence of this signal may indicate that EPL will occur. Since EPL can be a very sensitive marker of environmental toxins (Hakim, R. B., et al., 1995) and is frequently used as an epidemiological marker of exposure, the finding of this epitope provides a powerful tool for monitoring the safety of the environment. In addition, this assay facilitates increasing the success rate of IVF infertility programs since the predictive value of the new measuring system would rapidly indicate successful approaches. Described herein is the novel and completely unexpected finding that successful pregnancies display a high content of unique isoforms of hCG that are maintained for the first few weeks of pregnancy and then rapidly decline as pregnancy progresses. Based on properties of the immunoassay system, it is hypothesized that these hCG isoforms may be hyperglycosylated. This is a striking observation never reported nor suspected earlier. Carbohydrate analyses (Elliot, M., 1997) demonstrate that C5 hCG employed as immunogen for antibody B152, contains two times the monoantenny content and three times the tri-antennary content of branch chain sugars as compared to the CR series of natural pregnancy urinary hCG. In addition, the O-linked carbohydrates are mostly tetrasaccharide instead of disaccharide in C5 as compared to CR 127 hCG. (CR 127 hCG is similar to the WHO preparation, the third international hCG standard, which was CR 119 hCG, prepared by Canfield and Birken twenty years ago but still in use today) (Birken, S., et al., 1991a). B152 recognizes C5 hCG much better than nicked CR127 hCG or non-nicked CR 127 hCG (Birken, S., et al., 1993). In addition, JAR cell type hCG is known to contain a similar array of carbohydrate moieties. It was found to be recognized by B152 similar to the early pregnancy isoforms in healthy pregnancies. The observation that the hCG isoform produced by JAR cells in culture (B152/B109 ratio) is similar to that found in early pregnancy hCG isoforms supports the hypothesis that the production of a type of hCG with a particular glycosylation pattern is a prerequisite for a viable pregnancy. This glycosylation pattern is not characteristic of the hCG of later pregnancy.

A variety of pregnancy disorders are testable. One category of patients consists of those women who experience a high rate of recurrent abortions. Even in populations with no known fertility problems, the total rate of pregnancy loss is 32% (EPL plus clinically recognized abortion) (Wilcox, A. J., et al., 1988). The risk of recurrent abortion increases with the number of spontaneous abortions experienced in the past, reaching an incidence of 32% after three consecutive abortions. (Hill, J. A., and Anderson, D. J., 1990). Probable causes of recurrent spontaneous abortion, comprising genetic, infectious, hormonal imbalance, or immunologic factors can be established in less than 60% of all spontaneous abortions, leaving 40+% of spontaneous abortions with a completely unestablished etiology. These facts, taken together with reports establishing that the administration of exogenous hCG can be an effective therapy in subjects with a history of recurrent spontaneous abortion (Quenby, S., and Farquharson, R. G., 1994; Harrison, R. F., 1985) lends support to the hypothesis that a disproportionate production of the ineffective isoforms of hCG in early pregnancy is a causal factor in both early pre-clinical loss as well as in spontaneous abortion.

A second category includes women undergoing embryo transfer. These patients provide several distinct advantages: The patients undergoing this procedure are not treated with crude hCG preparations, making measurement of hCG isoforms easy and decisive since all hCG forms derive from the embryo none from any injected hCG preparations. Second, is the opportunity to monitor the nature of the isoforms from day 9 of a successful pregnancy. Third, is the ability to obtain large volumes of urine to purify the early pregnancy isoforms to determine their structures. Fourth, since pregnancy loss is from 50% to 70% in this population, the loss can be defined as due to lack of the essential hCG isoform recognized by B152 or due to other causes. Comparison of early pregnancies in populations of women not undergoing in vitro fertilization procedures with those undergoing embryo implantation can, thus, assess whether pregnancy loss situations present similar or different patterns of hCG isoforms during the process. The mechanism of pregnancy loss in the general population as compared with the much higher rate of embryo loss in IVF programs may be different. Additionally, it has been established that the hCG produced in choriocarcinoma has differences in carbohydrate structures, sialic acid content and biological activity (Wide, L., and Hobson, B., 1987; Elliot, M., et al., 1997; Hussa, R. A., 1987). Since both the B151-B604* and B152-B207* assays incorporate monoclonal antibodies raised against an immunogen derived from choriocarcinoma, specimens may be evaluated from patients with gestational trophoblastic disease in order to determine whether the above assays recognize the hCG produced in these conditions with greater sensitivity and specificity than do assays based on the hCG of normal pregnancy, as is apparently the case for the hCG produced in testicular and ovarian cancer.

There are few reports of changes of carbohydrate content of hCG-related molecules during pregnancy. Blithe and colleagues studied free alpha subunit of hCG whose carbohydrate content differs from that of alpha within hCG by additional carbohydrate antennae and fucose. The carbohydrate of free alpha becomes increasingly complex in terms of more branches and higher content as pregnancy proceeds. It has also been reported that the quantity of fucose increased in both hCG and in free alpha as pregnancy proceeded (Skarulis, M. C., et al., 1992). Thus, the literature indicates increasing content and complexity of carbohydrate of hCG and free alpha subunits. However, immunological data using the B152 monoclonal antibody, implies a progression to simpler carbohydrate content during pregnancy. Since the beta COOH-region's O-linked carbohydrates may be involved in the epitope recognized by B152, it is conceivable that the carbohydrate structures of this region may be altered in a different pattern from the N-linked glycans studied by Blithe and colleagues (Skarulis, M. C., et al., 1992; Blithe, D. L., and Iles, R. K., 1995). Data from Skarulis et al. indicate that heterodimeric hCG may contain additional fucose but do not provide data that this late pregnancy hCG becomes hyperglycosylated as does free alpha.

Other studies indicated that the forms of hCG during EPL likely differ in biological activity from those hCG isoforms in successful pregnancies (Ho, H.-H., et al., 1997). The in vitro bioassay employed in those studies are unsuitable for large-scale studies and are not as reliable as the immunoassays described herein. Furthermore, it is likely that in vivo assays may give different results since in vitro and in vivo assays sometimes give completely disparate results. In this case, in vivo and clearance assays are most important in order to identify whether the hCG isoforms are truly more potent in the whole animal and to identify the reasons for the increased potency. Thus in vitro and in vivo bioactivities of the early pregnancy isoforms of hCG are highly significant.

Carbohydrate differences is a widely accepted explanation for variations in biological to immunological ratio such as the forms observed by various studies of EPL (Ho, H.-H., et al., 1997). Various studies (Grotjan, H. R. J., and Cole, L. A., 1989; Hoermann, R., 1997; Stanton, P. G., et al., 1993; Szkudlinski, M. W., et al., 1995, Thotakura, N. R., et al., 1994.; Szkudlinski, M. W., et al., 1993), have shown that sialic acid differences are an explanation for such heterogeneity in biological activities of glycoprotein hormones. These studies have also confirmed the dogma that in vitro biological activities can yield the opposite results from in vivo studies because of altered metabolic clearance rates in the latter studies. Thus, more acidic (more highly sialylated)

forms of gonadotropins are more biopotent in the whole animal because of prolonged circulating half-lives. The same molecules may appear less potent in in vitro assays due to greater acidity, greater negative sialic acid content. Hoermann et al. (Hoermann, R., et al., 1997) demonstrated the exclusion of many of the acidic circulating hormone forms from the urine, thus, prolonging their half-lives. The pI pattern of normal pregnancy as well as trophoblastic cancer hCG in serum is quite different from that of urine. Since the studies described herein indicate that EPL hCG isoforms have reduced in vitro biological activity, this finding cannot be explained solely by what is known of biological activity and sialic acid content. Early pregnancy isoforms recognized by monoclonal antibody B152 may be more potent in vivo by virtue of prolonged half-life they may then display increased signal transduction at the receptor as well. This may be explained by a hyperglycosylated form of hCG which is not hypersiaylated. In this case, the extra sugar portion would help prolong circulating half-life of a more basic pI form of hCG which also has increased in vitro bioactivity.

Example 4

Diagnosis of Gestational Trophobloast Disease.

An important application of the B152 (early hCG isoform)/B109 (late hCG isoform) ratio analysis described herein above is in the very early (and facile) diagnosis of gestational trophoblast disease. Examples of gestational trophopblast disease include choriocarcinoma or hydatidiform mole. In normal pregnancy, the ratio of B152/B109 of the two isoforms of hCG rapidly decreases, eventually inverting. In gestational trophoblast disease including choriocarcinoma or hydatidiform mole, the ratio is initially higher than found in normal pregnancy, but does not diminish during the course of the apparent pregnancy. This approach provides a highly sensitive and specific diagnostic marker for gestational trophoblast disease.

Other pregnancy disorders in which hCG levels are abnormally high or abnormally low include Down's syndrome or other aneuploid pregnancies, ectopic pregnancy, preeclampsia, and intrauterine growth retardation. Because the hCG production in these conditions is quantitatively abnormal compared with normal pregnancy, an altered ratio of the hCG isoforms identified by B152 (early hCG isoform) and B109 (late hCG isoform) can be detected.

Thus, the dual isoform analysis (B152/B109) further provides a method for diagnosing pregnancy disorders and gestational trophoblast disease.

Materials And Methods

Hormones

The non-nicked hCG isolated from the CR127 preparation of hCG was used as a standard in both assays (Birken et al. 1993). The pituitary hCG was isolated as described (Birken et al. 1996). C5, a 100% nicked hCG having extra sugars on both N- and O-linked carbohydrate moieties, purified from the urine of a choriocarcinoma patient (Elliott et al. 1997), was supplied by Dr. Laurence Cole (Yale. University School of Medicine). Although the C5 immunogen used in the development of B152 antibody was 100% nicked hCG isoform (i.e. had cleavages in the peptide backbone of loop 2 of the b subunit) the antibody did not discriminate nicked from non-nicked hCG (O'Connor et al. 1998).

The same serial dilutions of non-nicked hCG, pituitary hCG and C5 were used for binding characterization in hCG assays. Hormone concentrations of initial stock standards solutions were determined by amino acid analysis.

Immunoradiometric Assays (IRMA)

The methodology used in the construction and validation of the B109-B108* assay has been fully described elsewhere (O'Connor et al. 1988). The B152-B207* assay has also been characterized O'Connor et al. 1998). Both assays were performed with slight modification of the published procedure: the capture antibody was adsorbed onto the wells of microtiter plates (Immulon IV, Dynatech, Chantilly, Va.) by incubating a 5 µg/ml solution (B109-B108* assay) or 25 mg/ml solution (B152-B207* assay) in coating buffer (0.2 M bicarbonate, pH 9.5) overnight at 4 C. The coating antibody solution was aspirated, the plates washed (wash solution: 0.9% NaCl, 0.05% Tween 20) and blocked with a 1% solution of BSA in PBS with 0.1% sodium azide. Following incubation with the BSA solution (minimum 3 hours at room temperature) the blocking solution was removed, the wells again washed with wash solution and 200 ml/well of the appropriate hCG standards were added in phosphate buffer B (PBS with 0.1% bovine gamma globulin and 0.1% sodium azide). After overnight incubation at 4 C., the plates were again aspirated and washed. The 200 ml (50,000 cpm-100, 000 cpm) of $^{125}$I—labeled antibody was added to the wells which were again incubated for 24 h at 4 C. The tracer was aspirated, the plates washed with wash solution, the individual wells placed in glass tubes and the radioactivity determined in a Packard Cobra gamma counter. Doses were determined by interpolation from a smoothed spline transformation of the data points.

All samples were stored frozen at −20 C. prior to assay. Because extreme values of sample pH may interfere with antibody binding, the urine pH was adjusted with 1.0 M Tris (pH 9.0), 50 µl/ml urine prior to assay, so that the final pH was in the range of 7-7.4 (O'Connor et al. 1988). Intra-assay variation was 6% for both assays, inter-assay variation was 12% for B109-B108* and 13% for B152-B207* assays. Sensitivity (least detectable dose) defined as +2SD from the zero calibrator, was 1 fmol/ml for the B109-B108* assay and 2.2 fmol/ml for B152-B207* assay.

Patients Samples

Urine samples from IVF patients were a gift from Dr. L. Cole. They included spontaneous abortion (n=14, range of gestational age 1.8-4.1 weeks from ET—embryo transfer), ectopic pregnancies (n=7, gestational age 2.3-4 weeks) and normal pregnancy controls (n=65, encompassing the range 0.6 to 5.4 week from ET). Some of the normal pregnancy urine samples throughout the pregnancies were also obtained from Dr. Cole. Others were obtained from the clinical practice of collaborating physicians at Columbia Presbyterian Medical Center (CPMC) (Total n=103). Matched serum/urine samples from the first (n=12) and the third (n=11) trimesters were provided by Dr. Amalia Kelly at CPMC. Trophoblast disease serum (n=17) and urine (n=28) samples were obtained from Dr. Cole, but were collected by Dr. Edward Newlands (Charing Cross Hospital, London, UK). All specimen collection protocols were approved by the appropriate Institutional Review Board.

Statistical Analysis

Polynomial regression models of log transformed hormone ratios were used to describe the relationship between the change in ratio as a function of gestational age in normal pregnancy. A paired t-test was used to evaluate the relationship between matched serum and urine hormone ratios. Analysis of covariance (ANCOVA) was used to describe the time adjusted relationship of hormone values in ectopic pregnancy and spontaneous abortion to those of normal pregnancy.

Urine Processing

Twenty-four hour urine samples are collected from women undergoing embryo transfer as well as women in early natural pregnancy. The urine is refrigerated during the collection procedure. After delivery of the urine to the laboratory, sodium azide is added to 1 g/liter. Women undergoing in vitro embryo transfer are not pre-treated with hCG. Thus, all hCG which appears in their blood or urine is derived from the embryo (except for the small amounts of pituitary hCG present in all people). Raw urine is freed from particles by centrifugation followed by Pellicon filtration through a 0.45 micron membrane. Next, the procedure is to concentrate the urine with a Pellicon (Millipore) system which concentrates as much as 30 liters to 500 ml overnight (4° C.) using a 3,000 MW cutoff membrane. Smaller volumes can be concentrated in less that two hours. Next, the urine is desalted and delipidated by passage through a large volume of Sephadex G25 in 0.1 M ammonium bicarbonate. This step greatly increases the binding of CG to immunoaffinity columns. The desalted urinary concentrate is next size fractionated on the Pharmacia HiLoad Superdex 200 and the hCG and hCG subunit peaks are identified by specific immunoassays (O'Connor, J. F., et al., 1994) and the appropriate fractions are pooled and dried. The hCG and hCG subunits are purified from the gel filtered urine concentrate by immunoaffinity on insolubilized hCG antibody columns as described but with the use of either 4 M guanadine (0.1 M tris acetate, pH 5) or ammonium thiocyanate as eluant to decrease loss of sialic acid from the hormone. Alternatively, hCG is purified by conventional chromatographic procedures, anion exchange and hydrophobic chromatography. The subunits are separated on reverse phase HPLC using a 0.01 M sodium phosphate, pH 5 buffer and acetonitrile, after incubation in 4 M guanadine, 0.1 M tris acetate, pH 5. A third method is final purification and separation of the hCG subunits on SDS PAGE electrophoresis followed by electroblotting to PVDF. The PVDF band can be subjected to protease digestion to release peptides and glycopeptides which can be separated on reverse phase HPLC in neutral pH 5 buffers.

Separation of Glycopeptides from Isolated hCG subunits.

To facilitate isolation of the glycopeptides from the hCG subunits, the subunits are both tryptic digested and the products of digestion are separated on reverse phase HPLC (using a pH 5 buffer). This procedure results in removal of the large beta COOH-terminal peptide which contains O-linked sugars. It also releases small, non glycopeptides from both subunits (Pollak, S., et al., 1990, Birken, S., et al., 1987; Birken, S., et al., 1986). Next, the main disulfide-linked core of each hCG subunit, is reduced and carboxymethylated, and separated on reverse phase HPLC at pH 5. At this stage, large peptides are isolated, including the glycopeptides. Each separated glycopeptide is redigested with trypsin and re-separated on HPLC at pH 5. These glycopeptides are next employed for two different methods of sugar chain analysis. One method is the approach of releasing the oligosaccharides by enzymatic digestions using PNGase F for the N-linked glycans. The released glycans can be separated from the peptides by ethanol precipitation, desialyated with neuraminadase, and separated directly on a Dionex Carbopac PA-100 column. Oligosaccharide standards are available from Dionex, Oxford Glycosystems and other companies for calibrating column elution times for various glycans (Hardy, M. R., and Townsend, R. R., 1994, Rohrer, J. S., et al., 1993, Weitzhandler, M., et al., 1993; Townsend, R. R., et al., 1989). Confirmation of the released structures is obtained by performing carbohydrate compositional analysis of eluted glycan peaks as well as performing digestions with specific glycosidases and rechromatographing the modified glycan on the Dionex system (Hardy, M. R., and Townsend, R. R., 1994; Rohrer, J. S., et al 1993; Weitzhanlder, M., et al., 1993; Townsend, R. R., et al., 1989; Townsend, R. R., et al., 1991; Townsend, R. R., et al., 1989; Hardy, M. R., and Townsend, R. R., 1989; Townsend, R. R., et al., 1988; Hardy, M. R., et al, 1997; Hardy, M. R., and Townsend, R. R., 1988; Dionex, 1997; Spellman, M. W., 1990; Kumarasamy, R., 1990). The newly modified glycan can be observed to elute at the same time as the appropriate standard oligosaccaharide and, in addition, the released monosaccharide can frequently be identified as well (Dionex, 1997). Structure determination is facilitated by the use of specific glycosidases for branch chain cleavage as well as for digestion of individual sugars from each of the branch chains. For example, Endo H cleaves high mannose type and hybrid oligosaccharide chains while glycosidase Endo F2 cleaves biantennary complex types and PNAase F cleaves tri and tetra-antennary chains down to the N-Asn bond.

Competitive Receptor Bindina And In Vitro Bioassay

Bioassays are performed with recombinant-engineered CHO cells transfected with the human receptor to LH/CG Cells are maintained in Ham's F-12 medium, 4 mM Glutamine, 400 ug/ml G418 (Gibco), 5% fetal calf serum, 100 IU/ml penicillin, 100 ug/ml streptomycin. The cells are removed from the flask surface by versene only.

A competitive receptor assay constructed as follows: The receptor binding assay mixture contains 100 ul of the appropriate dilution of serum/urine samples or hCG dilutions for standard curve, 100 ul of $^{125}$-I-hCG (50,000-100,000 cpm) in buffer A(PBs/0.1% BSA) and 100 ul of CHO cells (2×10 cells in PBS). The mixture is incubated at 37° C. with slight shaking followed by centrifugation for 10 minutes at 750×g. The supernatant is aspirated and the cell pellet is counted in gamma-counter.

In Vitro Bioassay. Transfected CHO cells are seeded (200,000 cells/well) into a 24 well plate in culture medium and incubated for 2-3 days until the cells reach confluence. Non-transfected CHO cells are included to monitor non-specific response. The medium is removed and replaced with medium containing 1 mM isobutylmethylxanthine with appropriate dilutions of tested serum or urine. The plates are incubated at 37° C. for two hours. The supernatant is removed, and the wells washed with hank's balanced salt solution. The intracellular cAMP is extracted with 95% ethanol, which is diluted 1:5, (or up to 1:40, depending on cAMP content) in assay buffer provided by the cAMP kit (New England Nuclear). cAMP assay is performed according to manufacturer's instructions. Response is normalized to well protein content (BCA protein assay kit, Pierce, Rockford, Ill.).

In vivo bioassay is determined by the uterine weight assay in immature female mice, following the procedure of Wide and Hobson (Wide, L., and Hobson, B., 1987). The mice are injected subcutaneously with one third of the total dose of gonadotropin on three consecutive days and killed 72 hours after the first injection. Uteri are dissected free from mesentery, fat and oviducts, blotted to remove intrauterine fluid and weighed to the nearest 0.1 mg. Five to ten mice are used at each of these dose levels. The hCG standard preparation used is a nicked hCG. This material may be run concurrently with specimens isolated from first and third trimester pregnancy. Sham saline injection may be used as a control. The response signal is the log mouse uterine weight.

Clearance Of hCG isoforms. The clearance of hCG is determined in the rat. Blood (200 ul/sample) is obtained at 0, 120, 240, 360 and 480 minutes post injection, from an indwelling catheter in an catheterized external jugular vein, following the procedure described by Newman et al. (Newman, C. B., et al., 1985) and Brown and Hedge (Brown, M. R., and Hedge, G. A., 1972). Briefly, adult male Sprague-Dawley rats (Charles River Laboratories, Wilmington Mass.), wt 175-225 g, are given free access to food and water. Rats are handled for acclimatization for one week after arrival, and several days before the hCG infusion, the rats are cannulated under pentobarbital anesthesia. A 21 gauge stainless steel cannula is inserted into the one external jugular vein. The placement of the catheter allows for the collection of blood from the unrestrained, unstressed rat. After the animals have recuperated from the cannula implacement an hCG isoform is injected (10 µg/ml sterile saline) through the cannulated vein. Blood samples are obtained at the four time intervals listed above. The blood is allowed to clot and the serum separated and stored at $-80°$ C. for immunometric assays specific for different hCG isoforms.

Clearance rate of the isoforms of hCG from the circulation of the rat are estimated by computer fitting the concentration data to an equation of the general form:

Concentration=$Ae^{-\alpha t+Be-\beta t}$ at time t; A and $\alpha$ are parameters of the rapid component and B and $\beta$ are parameters of the slow component. The metabolic clearance rate (MCR) is calculated as MCR=Dose/(A/$\alpha$+B/$\beta$) and the initial volume of distribution is calculated from $V_d$=Dose/(A+B). The MCR is normalized to body weight for statistical analysis, which is performed using ANOVA with Duncan's range test for determination of significance (Cassals, J. W., et al., 1989).

Mice. The mouse species used in the experiments described herein are Balb/c mice, aged 12-20 weeks old and adult Sprague-Dawley rats of either sex. Mice used for the production of monoclonal antibodies through ascites and for the determination of in vivo biological activity as described. Balbc/c mice are used because hybridoma cell lines were developed using Balb/c splenocytes.

EXPERIMENTAL DETAILS FOR THE SECOND SERIES OF EXPERIMENTS

Human Chorionic Gonadotropin exists in blood and urine as a variety of isoforms one of which contains peptide bond cleavages within its beta subunit loop 2 is referred to as nicked hCG (hCGn). This is hCG isoform appears to be more prevalent in the urine of patients with certain malignancies and possibly in some disorders of pregnancy. Until now, only indirect immunoassays could be used to quantify hCGn. We report the development of two monoclonal antibodies to a form of hCGn isolated from a choriocarcinoma patient. This hCG isoform was not only 100% nicked but also contained 100% tetrasaccharide-core O-linked carbohydrate moieties in its beta COOH-terminal region. Two-site immunometric assays have been developed using these new antibodies, B151 and B152. The former exhibits good specificity for hCGn independent of the source of the hCGn, that form excreted by choriocarcinoma patients or the form of hCGn form normal pregnancies. The latter antibody, B152, is sensitive to the carbohydrate moieties and possibly other differences in hCG isoforms but not for nicking of the beta subunit. These two immunometric assays provide potential novel diagnostic tools for direct measurement of hCG isoforms which could not be accurately quantified earlier before development of the assays using these newly generated antibodies.

Human Chorionic Gonadotropin (hCG) is a glycoprotein hormone produced by trophoblast cell of the placenta. The measurement of this hormone in blood or urine is the basis of all pregnancy tests. It is secreted by the trophoblast starting very early in pregnancy and functions to maintain steroid production by the corpus luteum until the placenta takes over that function later in pregnancy (1). There has been much recent interest in measurement of the hormone or its subunits or fragments for purposes other than the diagnosis of pregnancy such as monitoring of therapy for hCG-secreting malignancies (1), tests for indication of Down syndrome or other genetically-abnormal pregnancies (2-11), ectopic pregnancies (12), etc. HCG appears in urine in a variety of forms including free subunits, heterodimeric hCG with peptide bond cleavages in loop 2 of its beta subunit (known as nicked hCG), free nicked beta subunits, and the beta core fragment (13-16). The nicked form of heterodimeric in hCG has been reported to be present in blood as well as urine and is known to have much reduced immunochemical recognition by some antibodies directed to heterodimeric hCG as well as greatly reduced biological activity (13, 16-17). There are reported associations between increased nicking of hCG with certain hCG-secreting malignancies (18,19)

There are no satisfactory direct immunoassays for the nicked form of hCG nor for the nicked form of free hCG beta subunit. All measurements to date have been conducted with subtractive assay procedures or immunoassays which include scavenger antibodies (20-22). We report here the development of two antibodies of distinct specificity, using as immunogen the form of hCG produced by a single individual with choriocarcinoma. This particular hCG isoform was 100% nicked and hyperglycosylated both in its N and O-linked carbohydrate moieties. One resultant antibody, B151, displays significant preference towards binding to its choriocarcinoma hCG immunogen and does not recognize the nicked characteristic. Immunoassays developed using B152 are of special interest in their enhanced recognition of hCG isoforms more prevalent in preeclampsia and Down syndrome (23,24). B152 also appears to detect an hCG isoform associated with healthy pregnancies as juxtaposed to those pregnancies destined to fail early which have little of this isoform (25).

Results

Characteristics Of Antibodies

A variety of hCG isoforms were employed to characterize the new antibodies described in this report and the nomenclature and characteristics of each of the reagents employed is summarized in FIG. 11. The carbohydrate groups in these hCG isoforms as well as the percent nicking were analyzed in an earlier study (26) and are directly relevant for defining the nature of these new antibodies in this report.

Two antibodies designated B151 and B152 were selected by the use of radiolabeled hCG isoforms, chorioCG C5 and pregnancy hCG CR127. Each displayed preferential binding to C5 as compared to CR 127 since this was the selection criterion. However, upon performing liquid phase immunoassays and calculating affinity constants, it was clear that these two antibodies were very different in specificity (FIG. 12). It was found that antibody B151 had one order of magnitude higher affinity both for C5, which is nicked and hyperglycosylated choriocarcinoma hCG, and for CR127 hCGn (813) as compared to CR 127 hCG or nick-free CR 127(314) (See FIG. 11 for reagent descriptions). B151 was clearly an antibody with a strong preference for binding to various forms of nicked hCG. Antibody 152 was different in that although it displayed one order of magnitude preference for C5 hCG over CR127 hCG, it recognized the nicked and non-nicked forms of CR 127 hCG, hCG derived from normal pregnancies, to an equal extent.

Liquid Phase Assays

FIG. 8 shows potency comparisons of liquid phase immunoassays of both B151 and B152 antibodies comparing competitors: 1. standard CR 127 pregnancy hCG (which has a 20% content if nicked hCG); C5 chorio CG (100% nicked and hyperglycosylated); 3. 813, nicked CC made from CR 127 by purification, and 4. 814, non-nicked hCG derived from CR 127. The labeled ligand was C5 chorio CG. It is apparent that B151 (FIG. 8A) shows a preference for nicked forms of hCG. C5 chorio-CG or 813 hCGn bind with similar affinities. The slightly lower potency of 813 hCGn may be ascribed to its 20% contamination with non-nicked hCG. B152 only shows preference to C5, the hyperglycosylated chorio CG (FIG. 8B). 813 hCGn is no more potent a competitor than nick-free 814 hCG.

Immunometric Two Site Assays

A variety of two site antibody formats were tested. FIG. 13 displays these results. It is apparent that B151 cannot bind simultaneously with antibodies (designated by us as site IV) (27) to the beta subunit and beta subunit core (B201 and B204) nor with antibodies directed towards the determinant which exists in heterodimeric hCG as represented by antibody B109 (site III, to which A109 also belongs) (27). In contrast, a general beta antibody which binds to the most common and potent hCG antigenic site previously designated by us as site IT (BiOS and B207) binds well simultaneously with both B151 and B152 antibodies. B152 binds simultaneously to all antibodies tested except for those to the beta COCH-terminal region (CTP) (28) in contrast to B151 which binds well to CTP antibodies. B151 may represent a newly revealed hCG epitope which only exists on nicked hCG as reported in this manuscript.

Using B152 as capture and B207 or B108 as detection antibody, produces an assay which measures all normal pregnancy forms of hCG (both intact and nicked and beta subunit) to a similar extent but prefers binding to the form of hCG or beta subunit from its immunogen, C5. As predicted earlier from the liquid phase studies, this assay does not prefer nicked forms of hCG but hyperglycosylated forms of hCG such as C5. B152 and CTP 104 as well as several other monoclonal antibodies to the COOH-terminal region of HCG beta cannot bind simultaneously to C5, implying that this region is part of or very close to the epitope of B152. These data taken together with the apparent B152 preference for hyperglycosylated hCG, implies that the carbohydrate of the CTP region may be part of the B152 epitope. Further studies of the behavior of B152 in two-site assays confirm this hypothesis as detailed below.

Characteristics of the B152-B207-I$^{125}$ radioimmunometric two-site assay

Figure 9A:
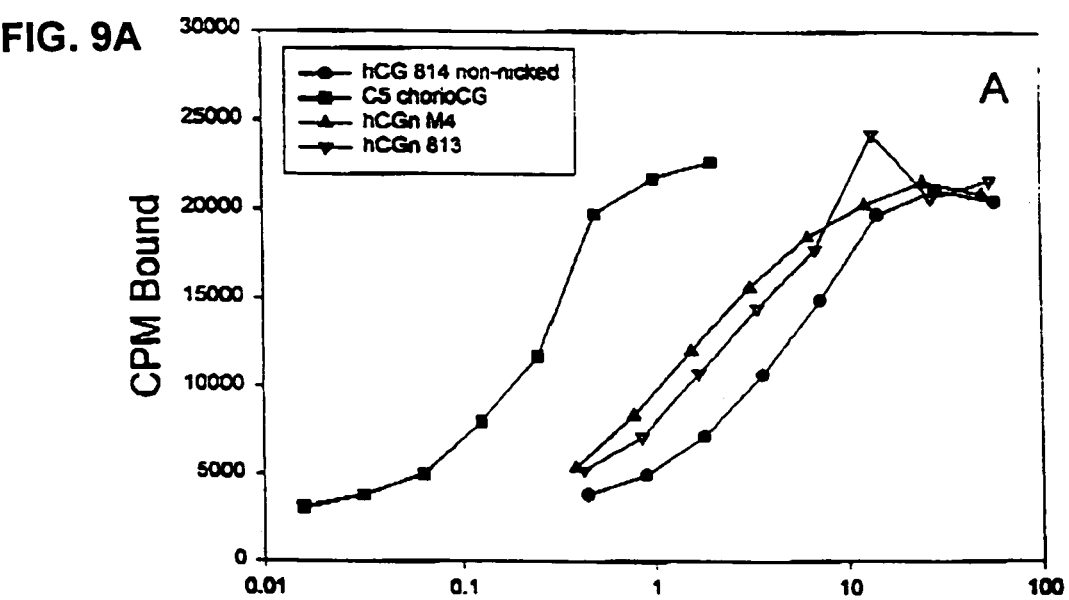
Figure 9B:
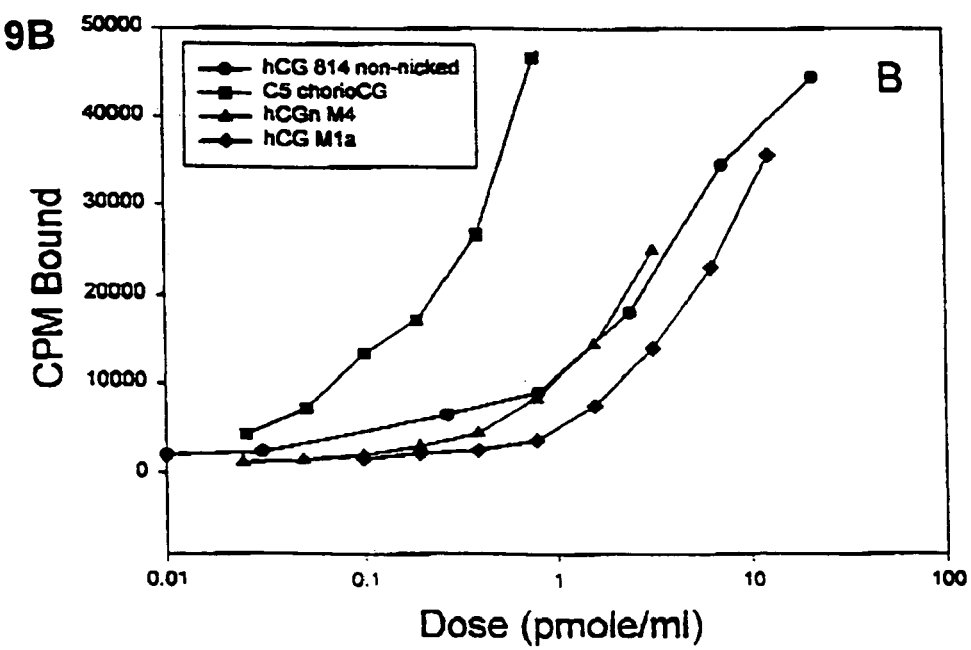
Figure 10:
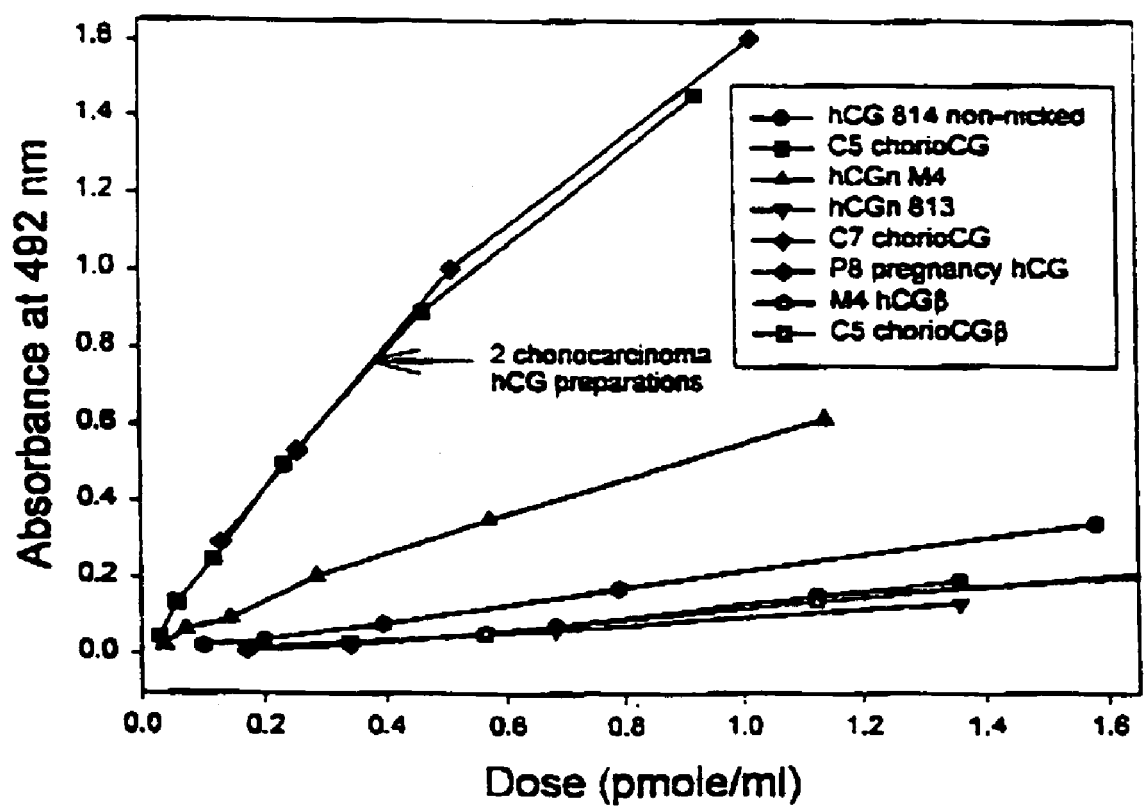

In order to better understand what this assay is measuring, we compared the relative binding potencies of a series of isoforms of hCG shown in FIG. 9 (also see methods) 1. C5, choriocarcinoma hCG 2. 814, non-nicked hCG. 3. 813, nicked hOG (80% nicked). 4. M4 mole-derived hCG, 98% nicked hCG with negligible hyperglycosylation. 5. MIA hcG, non-nicked and not significantly hyperglycosylated but missing 80% of the hCG beta COOR-terminus. The B152 two-site assays prefers to bind to C5, its immunogen, but shows nearly equal recognition of both 813 and 814, nicked and non-nicked hCG of normal pregnancy. This confirms that B152 does not display significant preference for the nicked form of hCG but rather for the form with carbohydrate differences. This is also confirmed by the potency of M4 which is also 100% nicked as in C5 but is not hyperglycosylated and displays a potency similar to CR127 hCG whether nicked or non-nicked. MIA is the least potent ligand and is the only one missing most of its beta COOR-terminal peptide confirming the role of this region in the B152 epitope.

In order to further explore the nature of the B152 binding site, a commercially available peroxidaselabeled general hCGβ antibody (4001) was employed as a detection antibody in a two-site enzyme immunometric system. Eight different hCG forms were evaluated in this system illustrated in FIG. 10. Results are analyzed in terms of relative immunopotency (based on the slope of the regression line) in FIG. 14. Linear regression correlation analysis was performed to compare the relationship of the immunopotencies of preparations 814, C5, M4, C7 and P8 one at a time with the carbohydrate differences (FIG. 11) as well as nicking differences among the 5 heterodimeric isoforms of hCG. The correlation results for each comparison are as follows: 1. Tetrasaccharide O-linked core: $R^2=0.9147$ P=0.0108, significant; 2. Triannentnary branched moieties N-linked on β: $R^2=0.3062$ P=0.3332, not significant; 4. Sialic acid N-linked on β: $R^2=0.2289$ P=0.4149, not significant; 5. Percent nicking on β subunit: $R^2=0.0984$ P=0.6072, not significant.

To summarize this analysis, the immunopotency of hCG is isoforms measured with B152 as a capture antibody in a two site assay correlates best with hyperglycosylated core moieties of both O and N-linked amino acids but not with sialic acid residues not with the degree of nicking of the β subunit.

Discussion

The various isoforms of hCG have received increasing attention during recent years for their potential diagnostic value in problem pregnancies such as Down syndrome, preeclampsia, trophoblastic diseases and early pregnancy loss. Nicked hCG at high concentrations has been associated with trophoblastic disease and other abnormal states of hCG production. Although nicked hCG has been measured by a variety of qualitative techniques such as immunoblotting, as well as by direct isolation and sequence analysis of such hCG isoforms from urine, it is only recently that some investigators have been measuring nicked forms of hCG by a variety of subtractive immunoassays or non-specific hCG assays with the addition of scavenger antibodies since direct, relatively specific antibodies were not available (22;29). We had earlier shown that our commonly used antibody, B109, to heterodimeric hCG reacted poorly to nicked forms of hCG and this antibody was employed by other groups in subtractive methods in attempts to quantify the content of nicked hCG in blood and urine(22;29).

In this report, we described development of two antibodies produced using choriocarcinoma-derived nicked hCG as immunogen. This led to a direct assay for nicked hCG. By employing a nicked, hyperglycosylated form of hCG from a single choriocarcinoma patient, we have developed two antibodies with distinct specificities. One antibody (B151) prefers binding to nicked forms of hCG, regardless of the origin of the hCG molecule normal pregnancy or choriocarcinoma). Nick-free CR127 hCG has the lowest affinity to this antibody as would be expected for a nick-directed antibody. While B151 was directed towards an epitope dependent upon peptide bond cleavages in beta loop 2, B152 binding was not affected by peptide bond cleavages within this loop. Since the main difference between C5 hCG and CR 127 hCGn was the hyperglycosylation of the former, it was inferred that B152 was chiefly a carbohydrate-directed antibody. When B151 is used as capture antibody and virtually any general beta antibody as detection antibody in a two site assay, little cross-reaction with hLH is observed. B151 cannot bind simultaneously with antibodies that are directed chiefly to the hCG beta core region (site IV such as B201 and B204) nor can the antibody bind with site III antibodies directed to heterodimeric hCG such as B109 or A109 but it can bind at the same time as antibodies to the beta COOH-region. B151 may represent a new hCG epitope revealed after nicking of beta loop 2. The creation of new epitopes by nicking of the hCG molecule has been reported by others (30).

The second antibody, B152, preferentially binds hCG with the type of carbohydrate modifications prevalent in choriocarcinoma CG C5 regardless of the state of the nicking of the polypeptide chain. This was shown by the measurement of the relative immunopotencies of several well characterized hCG isoforms as compared to their contents of N and O-linked carbohydrate moieties, sialic acid, and percentages of nicking. A significant correlation of B152 binding to hyperglycosylated hCG isoforms but not to those w th sialic acid or nicking differences was demonstrated. Antibody B152 appears to have at least partial specificity towards the hCG beta COOH-terminal region. This is shown by failure of a monoclonal antibody to bind simultaneously with beta COOH terminal antibodies such as CTP 104. In studies of B152 as a two site assay, it was shown that hCG isoform MIA which is missing most of its COOH-terminal region binds poorly to B152.

Each antibody has a different application in accordance with its specificity. Up to the present time, only indirect assays were available to quantify nicked hCG, such as subtractive assays or assays with scavenger antibodies added. Development of B151 permitted formulation of direct assays for nicked hCG which have been applied in studies of early pregnancy (25,31). These measurements may have diagnostic applications for certain cancers (18-19) and in the detection of Down Syndrome (22). Application of the B152 antibody resulted in development of assays which can detect differences in the carbohydrate portion of hCG. Major potential applications of this antibody include detection of Down Syndrome (23) and recognition of pregnancies destined for early pregnancy loss (25,32) This antibody is unusual since it is rare for carbohydrate discriminating antibodies to be developed to hCG. The only earlier such development was antibodies to the hCG beta COOH-terminal region by the use of the isolated peptide bound to carrier (28,33). It is of interest that at least part of the epitope of B152 is also directed towards the beta COOH-terminal region. As reported earlier, the C5 choriocarcinoma form of hCG was the only such hCG displaying 100% hexasaccharide structure on its O-Serine linked carbohydrate moieties in the beta COOH-terminal region. This may have resulted in production of this rare antibody. A second choriocarcinoma derived hCG isoform, C7, displayed 69% of this same O-linked core hexasaccharide structure and proved to be of similar potency as C5 with the B152 epitope.

In conclusion, we have produced two novel monoclonal antibodies each with potential clinical utility: B151 which can be used to measure nicked forms of hCG with better specificity than any antibody reported. B152 which is a unique antibody to a choriocarcinoma form of hCG and can discriminate hyperglycosylated from standard pregnancy hCG.

Materials and Methods

Hormones

Nick-free hCG (814) and nicked hCG (813) were prepared from pooled urine standard hCG (batch CR 127) by hydrophobic chromatography, as described previously (14). C8 hCG was purified from an individual with normal pregnancy, M1 and M4 hCG were both purified form individuals with gestational trophoblastic disease (hydatidiform mole), and C5 and C7 hCG form individual with malignant trophoblastic disease(choriocarcinoma), as described elsewhere (16,26). The N-terminal peptide sequences of the separated α-and β-subunits of CR127; P8, M1, M4, C5 and C7 hCG and complete N-and O-linked oligosaccharide structures have recently been published (26). Two peaks were observed by Sephacryl S100 HR chromatography during purification of hCG preparation M1. The peak eluting in the position of standard hCG (M1), and the peak eluting later (M1 A) were purified separately. M1 and M4 hCG were both purified from individuals with hydatidiform mole. They were isolated as described earlier (16).

Immunogens

Choriocarcinoma hCG designated C5 was isolated from a single patient as described earlier (16) and its complete carbohydrate analysis has recently appeared (26).

Immunization of Mice

Mice were immunized intraperitoneal with choriocarcinoma hCG preparation C5 diluted in saline (600 μg/mouse) and mixed 1:1 with Freund's adjuvant. After 3 consecutive immunizations (50 μg/mouse) at 3-4 week intervals, animals were retested for 3 months and then given an intraperitoneal booster immunization (34). Ten days after the last booster, the sera from mice were tested for binding (in liquid phase radioimmunoassays) to both iodinated CR 127 hCG and to iodinated C5 hCG.

Liquid Phase Assays

Liquid phase assays were performed using a solution of 80 μl 0.3M PBS with) 0.02% sodium azide, 50 μl tracer, 20 μl normal mouse serum, 50 μl 1% horse serum free of gamma globulin for titrations (when competition studies were performed, 50 μl of competitor solution were substituted to generate dose/response or Scatchard curves), 100 μl of diluted sera followed by incubation 1 hr at 37C. and then overnight at 4C. Next day 100 μl rabbit anti-mouse sera was added, incubated 10 min at 37 C, then 1 hr at ambient, then centrifuged, supernatdnt aspirated, and pellets counted. The mouse whose antisera had the greatest discrimination between binding of radiolabeled C5 and radiolabeled CR 127 hCG was sacrificed and their spleen's were used for hybridoma production. The methods and materials used for the fusion work were described earlier (27;34).

Characterization Of Antibodies

The cloned monoclonal antibodies, B151 and B152 were each studied in the liquid phase competitive radioimmunoassays using C5 as radiolabeled ligand and C5 and CR127 hCG as competitors. The method is as described under liquid phase assay method. Affinity constants were calculated by Scatchard plots as described earlier (35-37).

Two Site Assays

Two site assay testing was conducted at Yale University (enzyme immunometric) and Columbia University (radioimmunometric) as described earlier (24,37). Briefly, Immulon microtiter wells are coated with capture antibody, at a titer determined to provide the best combination of sensitivity and range. The plates were then washed and then blocked with 1% BSA in PBS. After a further wash, standards, clinical samples and controls were added to the coated wells (200 µL/well). Plates are incubated, then samples are removed and plates washed. Labeled antibody (either radio-labeled or peroxidase labeled) is then added, and plates incubated further. The response variable was generated by a gamma counter (Packard Instruments Cobra) or by absorption spectrophotometry as appropriate. A cubic spline curve is generated for standard values, and sample values read from this curve. Regression lines and all graphs were created using Sigmaplot 4.01 from SPSS software, Chicago, Ill. Linear regression analysis of immunopotency (FIG. 13) as compared to each of the carbohydrate difference and nicking differences of the hCG isoforms (FIG. 11) was accomplished in Instat 1998, Graphpad software, Inc., San Diego, Calif. USA.

REFERENCES FOR THE FIRST SERIES OF EXPERIMENTS

Amane, J., R. Nishimura, S. Sato, and A. Kobata. 1990. *Glycobiology.* 1:45-50.

Armstrong, E. G., P. H. Ehrlich, S. Birken, J. P. Schlatterer, E. Siris, W. C. Hembree, and R. E. Canfield. 1984. *J. Clin. Endocrinol. Metab.* 59:867-874.

Baenziger, J. U. 1994. FASEB J. 8:1019-1025.

Bahl, O. P., L. Marz, and W. R. Moyle. 1995. pp. 125-44. In Anonymous In: Dufau ML, Means AR, ed. Hormone binding and target cell activation in the testis. New York, Plenum Press, 1974.

Berger, P., Schwarz, S., Spottl, G., Wick, G. and Mann, K. (1993) Variants of human chorionic gonadotropin from pregnant women and tumor patients recognized by monoclonal antibodies. *J. Clin. Endocrinol. Metab.* 77, 347-351.

Birken, S., M. A. Kolks, S. Amr, B. Nisula, and D. Puett. 1987. *Endocrinclogy* 121:657-666.

Birken, S., Gawinowicz, MA, Kardana, A., Cole, LA. 1991. *Endocrinology* 129: 1551-1558.

Birken, S., Kovalevskaya, G., O'Connor, *J. Mol Cell Endocrinol,* 1996, 125:121-131.

Birken, S., M. A. Gawinowicz Kolks, S. Amr, B. Nisula, and D. Puett. 1986. *J. Biol. Chem.* 261:10719-10727.

Birken, S., Y. Chen, M. A. Gawinowicz, J. W. Lustbader, S. Pollak, G. Agosto, R. Buck, and J. O'Connor. 1993. *Endocrinology* 133:1390-1397.

Birken, S., Y. Maydelman, M. A. Gawinowicz, A. Pound, Y. Liu, and A. S. Hartree. 1996b. *Endocrinology* 137:1402-1411.

Blithe, D. L. and R. K. Iles. 199-5. *Endocrinology* 136: 903-910.

Braun, J. R., T. E. Willnow, S. Ishibashi, G. Ashwell, and J. Herz. 1996. *J. Biol. Chem.* 271:21160-21166.

Brown, M. R. and G. A. Hedge. 1972. *Neuroendocrinology.* 9:158-174.

Browne, E. S., M. V. Flasch, M. R. Sairam, and V. K. Bhalla. 1990. *Biochim. Biophys. Acta* 1033:226-234.

Cassals, J. W., Mann, K., Blithe, D. L., Nisula, B. C., Wehmann, R. E. 1989. *Cancer* 64:2313-2318.

Chang, P. L., Canfield, R. E., Ditkoff, E. C., O'Connor, J. F., Sauer, M. V., 1997. *Fertil. Steril.,* 1998, 69:412-414.

Chmielewski, C. 1992. *ANNA. J.* 19:34-38.

Cole, L. A., A. Kardana, P. Andrade-Gordon, M. A. Gawinowicz, J. C. Morris, E. R. Bergert, J. O'Connor, and S. Birken. 1991a. *Endocrinology* 129:1559-1567.

Cole, L. A., A. Kardana, F. C. Ying, and S. Birken. 1991b. *Yale J. Biol. Med.* 64:627-637.

Cole, L. A., A. Kardana, S. Y. Park, and G. D. Braunstein. 1993. *J. Clin. Endocrinol. Metab.* 76:704-710.

Cole, L. A., S. Birken, and F. Perini. 1985. *Biochem. Biophys. Res. Commun.* 126:333-339.

Diaz-Cueto, L., Barrios-de-Tomasi, J., Timossi, C., Mendez, J. P. and Ulloa-Aguirre, A. (996) More in-vitro bioactive, shorter-lived human chorionic gonadotrophin charge isoforms increase at the end of the first and during the third trimesters of gestation. *Mol. Hum. Reprod.* 2:643-650.

Dionex. 1997. *Technical Note* 42

Elliott, M. M., A. Kardana, J. W. Lustbader, and L. A. Cole. 1997. *Endocrine,* 7:15-32.

Ellish, N. J., Saboda, K, O'Connor, J, Nasca, P. C., Stanek, E F, Boyle, C. *Hum Reprod* 1996 11:406-412.

Fares, F. A., N. Suganuma, K. Nishimori, P. S. LaPolt, A. J. Hsueh, and I. Boime. 1992. *Proc. Natl. Acad. Sci. U. S. A.* 89:4304-4308.

Fein, H. G., Rosen, S. W. and Weintraub, B. D. (1980) Increased glycosylation of serum human chorionic gonadotropin and subunits from eutopic and ectopic sources: comparison with placental and urinary forms. *J Clin Endocrinol Metab* 50, 1111-1120.

Fiete, D., V. Srivastava, O. Hindsgaul, and J. U. Baenziger. 1991. *Cell* 67:1103-1110.

Grotjan, H. R. J. and L. A. Cole. 1989. In Microheterogeneity of Glycoprotein Hormones. H. R. J. Grotjan and L. A. Cole, editors. CRC Press, Boca Raton. 219-237.

Hakim, R. B., R. H. Gray, and H. Zacur. 1995. *Am. J. Obstet. Gynecol.* 172:1510-1517.

Hardy, M. R. and R. R. Townsend. 1988. *Proc. Natl. Acad. Sci. U. S. A.* 85:3289-3293.

Hardy, M. R., R. R. Townsend, and Y. C. Lee. 1997. *Anal Biochem* 1988 April 170(1):54-62, Hardy, M. R. and R. R. Townsend. 1989. *Carbohydr. Res.* 188:1-7.

Hardy, M. R. and R. R. Townsend. 1994. *Methods Enzymol.* 230:208-225.

Harrison, R. F. 1985. *Europ. J. Obstet. Gynec. reprod. Biol.* 20:159-168.

Hill, J. A. and D. J. Anderson. 1990. *Archsm. Immun. Ther. Exp.* 38:111-119.

Ho, H-H, O'Connor, J F, Overstreet, J W, Lasley, B L. *Early Pregnancy:Biology and Medicine,* 1997, 3:153-163.

Hoermann, R., G. Spoettl, M. Grossmann, B. Saller, and K. Mann. 1997. *J. Clin. Invest.* 71:953-960.

Hoermann, R., P. Berger, G. Spoettl, F. Gillesberger, A. Kardana, L. A. Cole, and K. Mann. 1994. *Clin. Chem.* 40:2306-2312.

Hussa, R. O. 1987. The Clinical Marker hCG. Praeger, New York.

Kagimoto, A., R. Sakakibara, N. Fukushima, N. Ikeda, and M. Ishiguro. 1995. *Biol. Pharm. Bull.* 18:8.10-817.

Kardana, A., G. D. Braunstein, and L. A. Cole. 1996. *Oncol. Res.* 8:13-16.

Kardana, A. and L. A. Cole. 1992. *Clin. Chem.* 38:26-33.

Karlsson, F. A., P. Burman, O. Kampe, J. E. Westlin, and L. Wide. 1993. *Acta Endocrinol. (Copenh)* 129:291-295.

Kawasaki, T. and G. Ashwell. 1976. *J. Biol. Chem.* 251:1296-1302.

Kovalevskaya, G, Birken, S, O'Connor, J, Schlatterer, J, Maydelman, Y, Canfield, R. *Endocrine,* 1995, 3:881-887.

Kumarasamy, R. 1990. *J. Chromatogr.* 512:149-155.

Lasley, B. L., P. Lohstroh, A. Kuo, E. B. Gold, B. Eskenazi, S. J. Samuels, D. R. Stewart, and J. W. Overstreet. 1995. *Am. J. Ind. Med.* 28:771-781.

Maack, T., C. H. Park, and M. J. F. Camargo. 1985. In The kidney: Physiology and pathophysiology. D. W. Seldin and G. Giebisch, editors. Raven Press, New York. 1773-1803.

Matzuk, M. M., A. J. Hsueh, P. Lapolt, A. Tsafriri, J. L. Keene, and I. Boime. 1990. [published erratum appears in Endocrinology 1990 Apr; 126(4):2204]. *Endocrinology* 126:376-383.

Moyle, W. R., O. P. Bahl, and L. Marz. 1975. *Journal of Biological Chemistry* 250:9163-9169.

Newman, C. B., S. L. Wardlaw, and A. G. Frantz. 1985. *Life Sci.* 36:1661-1668.

Nishimura, R., T. Kitajima, K. Hasegawa, K. Takeuchi, and M. Mochizuki. 1989. *Jpn. J. Cancer Res.* 80:968-974.

Nishimura, R., T. Utsunomiya, K. Ide, T. Kitajima, H. C. Chen, J. L. Strobel, R. 0. Hussa, and M. Mochizuki. 1987. *Jpn. J. Cancer Res.* 78:833-839.

Nishimura, R., K. Ide, T. Utsunomiya, T. Kitajima, Y. Yuki, and M. Mochizuki. 1988. *Endocrinology* 123:420-425.

O'Connor, J., G. Kovalevskaya, S. Birken, J. P. Schlatterer, D. Schechter, D. McMahon, and R. E. Canfield. 1998. *Hum. Reprod.* 13:826-835.

O'Connor, J. F., S. Birken, J. W. Lustbader, A. Krichevsky, Y. Chen, and R. E. Canfield. 1994. *Endocr. Rev.* 15:650-683.

O'Connor, J. F., J. P. Schlatterer, S. Birken, A. Krichevsky, E. G. Armstrong, D. McMahon, and R. E. Canfield. 1988. *Cancer Res.* 48:1361-1366.

Odell, W. D. and J. Griffin. 1989. *J. Clin. Endocrinol. Metab.* 69:528-532.

Odell, W. D. and J. Griffin. 1987. *N. Engl. J. Med.* 317:1688-1691.

Pollak, S., S. Halpine, B. T. Chait, and S. Birken. 1990. *Endocrinology* 126:199-208.

Puisieux, A., D. Bellet, F. Troalen, A. Razafindratsita, C. Lhomme, C. Bohuon, and J. M. Bidart. 1990. *Endocrinology* 126:687-694.

Quadri, K. H., J. Bernardini, A. Greenberg, S. Laifer, A. Syed, and J. L. Holley. 1994. *Am. J. Kidney Dis.* 24:416-420.

Quenby, S. and R. G. Farquharson. 1994. *Fertil. Steril.* 62:708-710.

Ravindranath, N., N. S. Srilatha, M. R. Sairam, and N. R. Moudgal. 1992. *Indian J. Exp. Biol.* 30:982-986.

Rohrer, J. S., G. A. Cooper, and R. R. Townsend. 1993. *Anal. Biochem.* 212:7-16.

Sairam, M. R. and L. G. Jiang. 1992. *Mol. Cell Endocrinol.* 85:227-235.

Sairam, M. R. 1989. *FASEB J.* 3:1915-1926.

Sairam, M. R., J. Linggen, and G. N. Bhargavi. 1988. *Biosci. Rep.* 8:271-278.

Skarulis, M. C., R. E. Wehmann, B. C. Nisula, and D. L. Blithe. 1992. *J. Clin. Endocrinol. Metab.* 75:91-96.

Spellman, M. W. 1990. *Anal. Chem.* 62:1714-1722.

Stanton, P. G., G. Poznek, P. G. Burgon, D. M. Robertson, and M. T. W. Hearn. 1993. *J Endocrinol.* 138:529-543.

Szkudlinski, M. W., N. R. Thotakura, I. Bucci, L. R. Joshi, A. Tsai, J. East-Palmer, J. Shiloach, and B. D. Weintraub. 1993. *Endocrinology* 133:1490-1503.

Szkudlinski, M. W., N. R. Thotakura, J. E. Tropea, M. Grossmann, and B. D. Weintraub. 1995. *Endocrinology* 136:3325-3330.

Taussky, H. H. 1954. *J. Biol. Chem.* 208:853-861.

Thotakura, N. R., M. W. Szkudlinski, and B. D. Weintraub. 1994. *Glycobiology.* 4:525-533.

Townsend, R. R., M. Hardy, J. D. Olechno, and S. R. Carter. 1988. *Nature* 335:379-380.

Townsend, R. R., P. H. Atkinson, and R. B. Trimble. 1991. *Carbohydr. Res.* 215:211-217.

Townsend, R. R., M. R. Hardy, and Y. C. Lee. 1989. *Methods Enzymol.* 179:65-76.

Townsend, R. R., M. R. Hardy, D. A. Cumming, J. P. Carver, and B. Bendiak. 1989. *Anal. Biochem.* 182:1-8.

Ulloa-Aguirre, A., Mendez, J. P., Cravioto, A., Grotjan, E., Damian-Matsumura, P. and Espinoza, R. (1990) Studies on the microheterogeneity of chorionic gonadotrophin secreted by the human cytotrophoblast in culture. *Hum. Reprod.* 5, 661-669.

Weitzhandler, M., D. Kadlecek, N. Avdalovic, J. G. Forte, D. Chow, and R. R. Townsend. 1993. *J. Biol. Chem.* 268: 5121-5130.

Wide, L. and B. Hobson. 1987. *Acta Endocrinol. (Copenh)* 116:465-472.

Wilcox, A. J., C. R. Weinberg, J. F. O'Connor, D. D. Baird, J. P. Schlatterer, R. E. Canfield, E. G. Armstrong, and B. C. Nisula. 1988. *N. Engl. J. Med.* 319:189-194.

Zinaman, M J, Clegg, E D, Brown, C C, O'Connor, J, Selevan, S G. *Fertil Steril.,* 1996, 65:503-509.

REFERENCES FOR THE SECOND SERIES OF EXPERIMENTS

1. Hussa, R. O. (1987) The clinical Marker hCG, Praeger, New York.

2. Forest, J.C., Masse, J., Rousseau, F., Moutquin, J. M., Brideau, N.A., and Belanger, M (1995) *Clin. Biochem.* 28, 443-449.

3. Spencer, K., Macri, J. N., Carpenter, P., Anderson, R., and Krantz, D. A. (1993) *Clin. Chem.* 39, 1064-1068.

4. Spencer, K., Aitken, D. A., Macri, J. N., and Buchanan, P. D. (1996) *Prenat. Diagn.* 16, 605-613.

5. Spencer, K., Muller, F., and Aitken, D. A. (1997) *Prenat. Diagn.* 17, 31-37.

6. Valerio, D., Aiellci, R., Altieri, V., and Fagnoni, P. (1996) *Minerva. Ginecol.* 48, 169-173.

7. Wald, N. J., Kennard, A., and Smith, D. (1994) *Ann. Med.* 26, 23-29.

8. Wald, N. J., Densem, J. W., Smith, D., and Klee, G. G. (1994) *Prenat. Diagn.* 14, 707-716.

9. Zimmermann, R., Reynolds, T. M., John, R., Spencer, K., Bartels, I., Coombes, E., and Trevor, S. (1996) *Prenat. Diagn.* 16, 79-82.

10. Bogart, M. H., Pandian, M. R., and Jones, O. W. (1987) *Prenat. Diagn.* 7, 623-630.

11. Bogart, M. H., Golbus, M. S., Sorg, N. D., and Jones, O. W. (1989) *Prenat. Diagn.* 9, 379-384.

12. Cole, L. A., T. Isozaki, and E. E. Jones. (1997) *Fetal. Diagn. Ther.* 12:336-339.

13. Birken, S., Gawinowicz, M. A., Kardana, A., and Cole, L. A. (1991) *Endocrinology* 129, 1551-1558.

14. Birken, S., Chen, Y., Gawinowicz, M. A., Lustbader, J. W., Pollak, S., Agosto, G., Buck, R., and O'Connor, J. (1993) *Endocrinology* 133, 1390-1397.

15. Birken, S., Kovalevskaya, G., and O'Connor, J. (1996) *Mol. Cell. Endocrinol.* 125, 121-131.

16. Kardana, A., Elliot, M. M., Gawinowicz, M. A., Birken, S., and Cole, L. A. (1991) *Endocrinology* 129, 1541-1550.

17. Cole, L. A., Kardana, A., Andrade-Gordon, P., Gawinowics, M. A., Morris, J. C., Bergert, E. R., O'Connor, J., and Birken, S. (1991) *Endocrinology* 129, 1559-1567.

18. Puisieux, A., Bellet, D., Troalen, F., Razafindratsita, A., Lhomme, C., Bohuon, C., and Bidart, J. M. (1990) *Endocrinology* 126, 687-694.

19. Nishimura, R., Utsunomiya, T., Ide, K., Kitajima, T., Chen, H. C., Strobel, J. L., Hussa, R. O., and Mochizuki, M. (1987) *Jpn. J. Cancer Res.* 78, 833-839.

20. Kardana, A. And Cole, L. A. (1992) *Clin. Chem.* 38, 26-33.

21. Kardana, A. And Cole, L. A. (1994) *J. Clin. Endocrinol. Metab.* 79, 761-767.

22. Rotmensch, S., Liberati, M., Kardana, A., Copel, J. A., Ben-Rafael, Z., and Cole, L. A. (1996) *Am. J. Obstet. Gynecol.* 174, 609-611.

23. Cole, L. A., Cermik, D., and Bahado-Singh, R. (1997) *Prenat.Diagn.* 17, 1180-1190.

24. Cole, L. A. and Omrani, A. Cermik E. Mahoney R. (1998) *Prenat. Diagn.* 18, 926-933.

25. O'Conner, J., Ellish, N. J., Schlatterer, J., and Kovalevskaya, G. (1998) *Prenat.Diagn.* 18, 1232-40.

26. Elliott, M. M., Kardana, A., Lustbader, J. W., and Cole, L. A. (1997) *Endocrine* 7, 15-32.

27. Krichevsky, A., Armstrong, E. G., Schlatterer, J., Birken, S., O'Connor, J., Bikel, K., Silverberg, S., Lustbader, J., and Canfield, R. (1988) *Endocrinology* 123, 584-593.

28. Krichevsky, A., Birken, S., O'Connor, J., Acevedo, H. F., Bikel, K., Lustbader, J., Hartree, A., and Canfield, R. E. (1994) *Endocrinology* 134, 1139-1145.

29. Cole, L. A., Kardana, A., Park, S. Y., and Braunstein, G. D. (1993) *J. Clin. Endocrinol. Metab.* 76, 704-710.

30. Hoermann, R., Berger, P., Spoettl, G., Gillesberger, F., Kardana, A., Cole, L. A. and Mann, K. (1994) *Clin. Chem* 40, 2306-2312.

31. Kovalevskaya, G., Birken, S., Kakuma, T., Schlatterer, J., and O'Connor, J.F. (1999) *Clin. Chem* 45, 68-77.

32. Kovalevskaya, G., Birken, S., Kakuma, T., and O'Connor, J. F. (1999) *J. Endocrinol.* 161:99-106.

33. Birken, S., Agosto, G., Amr, S., Nisula, B., Cole, L., Lewis, J., and Canfield, R. (1988) *Endocrinology* 122, 2054-2063.

34. Ehrlich, P. H., Moustapha, Z., Birken, S., Moyle, W. R., and Canfield, R. (1985) *Am. J. Reprod. Immunol. Microbiol* 8, 48-54.

35. Scatchard, G. (1949) *Ann. NY. Acad. Sci* 51, 660.

36. Moyle, W. R., Ehrlich, P. H., and Canfield, R. E. (1988) in Oxford Reviews of Reproductive Biology (Finn, C. A., Ed.), pp. 123 Clarendon Press, Oxford.

37. O'Connor J. F., Schlatterer J. P., Birken. S., Krichevsky A., Armstrong E. G., McMahon D., Canfield R. E. (1988) Cancer Res 48, 1361-1366.

What is claimed is:

1. A method for detecting non-trophoblast malignancy in a sample comprising:

(a) contacting the sample with a first antibody which specifically binds to the early pregnancy associated molecular isoform of hCG under conditions permitting formation of a complex between the antibody and the early pregnancy associated molecular isoform of hCG, wherein the first antibody is B152 produced by the hybridoma deposited with the American Type Culture Collection under Designation No. HB-12467 and the complex is detected by B207 antibody produced by the hybridoma deposited with the American Type Culture Collection under ATCC Designation No. PTA-1626;

(b) contacting the sample with a second antibody which specifically binds to intact non-nicked hCG without cross-reacting with the first antibody under conditions permitting formation of a complex between the second antibody and the early pregnancy associated molecular isoform of hCG;

(c) measuring the amount of complexes formed in steps (a) and (b; and (d) comparing the amount of complex formed in step (a) with the amount of complex formed in step (b), wherein a positive detection of complex formed in step (a) and a relative absence of complex formed in step (b) indicates the presence of non-trophoblast malignancy in the sample.

2. The method of claim 1, wherein the second antibody is B109 produced by the hybridoma deposited with the American Type Culture Collection under ATCC Designation No. PTA-1624.

3. The method of claim 1, wherein the complex formed in step (b) is detected by a detection antibody.

4. The method of claim 3, wherein the detection antibody is B108 produced by the hybridoma deposited with the American Type Culture Collection under ATCC Designation No. PTA-1625.

5. The method of claim 1, wherein the non-trophoblast malignancy is an ovarian malignancy or a prostate malignancy.

6. The method of claim 1, wherein the sample is a urinary sample or a blood sample.

* * * * *